US007647115B2

(12) United States Patent
Levin et al.

(10) Patent No.: US 7,647,115 B2
(45) Date of Patent: **\*Jan. 12, 2010**

(54) RENAL NERVE STIMULATION METHOD AND APPARATUS FOR TREATMENT OF PATIENTS

(75) Inventors: Howard R. Levin, Teaneck, NJ (US); Mark Gelfand, New York, NY (US)

(73) Assignee: Ardian, Inc., Palo Alto, CA (US)

( * ) Notice: Subject to any disclaimer, the term of this patent is extended or adjusted under 35 U.S.C. 154(b) by 538 days.

This patent is subject to a terminal disclaimer.

(21) Appl. No.: 11/144,173

(22) Filed: Jun. 3, 2005

(65) Prior Publication Data

US 2005/0228459 A1    Oct. 13, 2005

Related U.S. Application Data

(63) Continuation of application No. 10/408,665, filed on Apr. 8, 2003, now Pat. No. 7,162,303.

(60) Provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61N 1/00* (2006.01)
(52) U.S. Cl. ....................................... 607/44
(58) Field of Classification Search ............ 607/2, 607/44, 40–41; 604/21
See application file for complete search history.

(56) References Cited

U.S. PATENT DOCUMENTS

| | | | |
|---|---|---|---|
| 2,130,758 | A | 9/1938 | Rose |
| 2,276,995 | A | 3/1942 | Milinowski |
| 2,276,996 | A | 3/1942 | Milinowski |
| 3,043,310 | A | 7/1962 | Milinowski |
| 3,127,895 | A | 4/1964 | Kendall et al. |
| 3,181,535 | A | 5/1965 | Milinowski |
| 3,270,746 | A | 9/1966 | Kendall et al. |
| 3,329,149 | A | 7/1967 | Kendall et al. |
| 3,522,811 | A | 8/1970 | Schwartz et at |
| 3,563,246 | A | 2/1971 | Puharich et al. |
| 3,650,227 | A | 3/1972 | Sjostrand et al. |

(Continued)

FOREIGN PATENT DOCUMENTS

DE    3151180 A1    8/1982

(Continued)

OTHER PUBLICATIONS

Augustyniak, R.A. et al., "Sympathetic Overactivity as a Cause of Hypertension in Chronic Renal Failure," Journal of Hypertension, 2002, 20:3-9.

(Continued)

*Primary Examiner*—Mark W Bockelman
(74) *Attorney, Agent, or Firm*—Perkins Coie LLP

(57) ABSTRACT

A method and apparatus for treatment of heart failure, hypertension and renal failure by stimulating the renal nerve. The goal of therapy is to reduce sympathetic activity of the renal nerve. Therapy is accomplished by at least partially blocking the nerve with drug infusion or electrostimulation. Apparatus can be permanently implanted or catheter based.

53 Claims, 9 Drawing Sheets

U.S. PATENT DOCUMENTS

| | | |
|---|---|---|
| 3,670,737 A | 6/1972 | Pearo |
| 3,760,812 A | 9/1973 | Timm et al. |
| 3,774,620 A | 11/1973 | Hansjurgens |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage |
| 4,315,503 A | 2/1982 | Ryaby et al. |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,608,985 A | 9/1986 | Crish et al. |
| 4,649,936 A | 3/1987 | Ungar et al. |
| 4,671,286 A | 6/1987 | Renault |
| 4,674,482 A | 6/1987 | Waltonen et al. |
| 4,692,147 A | 9/1987 | Duggan |
| 4,715,852 A | 12/1987 | Reinicke et al. |
| 4,774,967 A | 10/1988 | Zanakis |
| 4,791,931 A | 12/1988 | slate |
| 4,816,016 A | 3/1989 | Schulte et al. |
| 4,852,573 A | 8/1989 | Kennedy |
| 4,865,845 A | 9/1989 | Eckenhoff et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,057,318 A | 10/1991 | Magruder et al. |
| 5,058,584 A | 10/1991 | Bourgeois |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,304,120 A | 4/1994 | Crandell et al. |
| 5,304,206 A | 4/1994 | Baker |
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,472,406 A | 12/1995 | de la Torre et al. |
| 5,478,303 A | 12/1995 | Foley-Nolan et al. |
| 5,494,822 A | 2/1996 | Sadri |
| 5,498,238 A | 3/1996 | Shapland et al. |
| 5,499,971 A | 3/1996 | Shapland et al. |
| 5,507,724 A | 4/1996 | Hofmann et al. |
| 5,507,791 A | 4/1996 | Sit'ko |
| 5,531,778 A | 7/1996 | Maschino et al. |
| 5,540,730 A | 7/1996 | Terry, Jr. et al. |
| 5,540,734 A | 7/1996 | Zabara |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,589,192 A | 12/1996 | Okabe et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,792,187 A | 8/1998 | Adams |
| 5,800,464 A | 9/1998 | Kieval |
| 5,807,306 A | 9/1998 | Shapland et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,861,021 A | 1/1999 | Thome et al. |

| Patent | Date | Inventor |
|---|---|---|
| 5,865,787 A | 2/1999 | Shapland et al. |
| 5,871,449 A | 2/1999 | Brown |
| 5,891,181 A | 4/1999 | Zhu |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,983,131 A | 11/1999 | Weaver et al. |
| 5,983,141 A | 11/1999 | Sluijter et al. |
| 6,006,134 A | 12/1999 | Hill et al. |
| 6,010,613 A | 1/2000 | Walters et al. |
| 6,026,326 A | 2/2000 | Bardy |
| 6,051,017 A | 4/2000 | Loeb et al. |
| 6,058,328 A | 5/2000 | Levine et al. |
| 6,058,331 A | 5/2000 | King |
| 6,073,048 A | 6/2000 | Kieval et al. |
| 6,077,227 A | 6/2000 | Miesel et al. |
| 6,086,527 A | 7/2000 | Talpade |
| 6,122,548 A | 9/2000 | Starkebaum et al. |
| 6,123,718 A | 9/2000 | Tu et al. |
| 6,146,380 A | 11/2000 | Racz et al. |
| 6,161,048 A | 12/2000 | Sluijter et al. |
| 6,178,349 B1 | 1/2001 | Kieval |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,238,702 B1 | 5/2001 | Berde et al. |
| 6,245,026 B1 | 6/2001 | Campbell et al. |
| 6,246,912 B1 | 6/2001 | Sluijter |
| 6,251,130 B1 | 6/2001 | Dobak, III et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,280,377 B1 | 8/2001 | Talpade |
| 6,287,304 B1 | 9/2001 | Eggers et al. |
| 6,287,608 B1 | 9/2001 | Levin et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |
| 6,306,423 B1 | 10/2001 | Donovan et al. |
| 6,326,020 B1 | 12/2001 | Kohane et al. |
| 6,326,177 B1 | 12/2001 | Schoenbach et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni et al. |
| 6,605,084 B2 | 8/2003 | Acker et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,635,054 B2 | 10/2003 | Fjield et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,749,598 B1 | 6/2004 | Keren et al. |
| 6,786,904 B2 | 9/2004 | Doscher et al. |
| 6,795,728 B2 | 9/2004 | Chomenky et al. |
| 6,845,267 B2 | 1/2005 | Harrison et al. |
| 6,850,801 B2 | 2/2005 | Kieval et al. |
| 6,865,416 B2 | 3/2005 | Dev et al. |
| 6,885,888 B2 | 4/2005 | Rezai |
| 6,916,656 B2 | 7/2005 | Walters et al. |
| 6,927,049 B2 | 8/2005 | Rubinsky et al. |
| 6,939,345 B2 | 9/2005 | KenKnight et al. |
| 6,958,060 B2 | 10/2005 | Mathiesen et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 2001/0044596 A1 | 11/2001 | Jaafar |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183684 A1 | 12/2002 | Dev et al. |
| 2002/0188325 A1 | 12/2002 | Hill et al. |
| 2002/0198512 A1 | 12/2002 | Seward |

| | | |
|---|---|---|
| 2003/0004549 A1 | 1/2003 | Hill et al. |
| 2003/0009145 A1 | 1/2003 | Struijker-Boudier et al. |
| 2003/0040774 A1 | 2/2003 | Terry et al. |
| 2003/0045909 A1 | 3/2003 | Gross et al. |
| 2003/0060848 A1 | 3/2003 | Kieval et al. |
| 2003/0060857 A1 | 3/2003 | Perrson et al. |
| 2003/0060858 A1 | 3/2003 | Kieval et al. |
| 2003/0100924 A1 | 5/2003 | Foreman et al. |
| 2003/0120270 A1 | 6/2003 | Acker |
| 2003/0150464 A1 | 8/2003 | Casscells |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0236443 A1 | 12/2003 | Cespedes et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0220511 A1 | 11/2004 | Scott et al. |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080459 A1 | 4/2005 | Jacobson et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2005/0288730 A1 | 12/2005 | Deem et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0089674 A1 | 4/2006 | Walters et al. |
| 2006/0116720 A1 | 6/2006 | Knoblich |
| 2006/0135998 A1 | 6/2006 | Libbus et al. |
| 2006/0136004 A1 | 6/2006 | Cowan et al. |
| 2006/0155344 A1 | 7/2006 | Rezai et al. |
| 2006/0189941 A1 | 8/2006 | Seward et al. |
| 2006/0190044 A1 | 8/2006 | Libbus et al. |
| 2006/0206149 A1 | 9/2006 | Yun |
| 2006/0229677 A1 | 10/2006 | Moffitt et al. |
| 2006/0235474 A1 | 10/2006 | Demarais |
| 2006/0265015 A1 | 11/2006 | Demarais et al. |

FOREIGN PATENT DOCUMENTS

| | | |
|---|---|---|
| EP | 0811395 A2 | 6/1997 |
| WO | WO-85/01213 | 3/1985 |
| WO | WO-91/04725 | 4/1991 |
| WO | WO-93/02740 | 2/1993 |
| WO | WO-93/07803 | 4/1993 |
| WO | WO-94/00188 | 1/1994 |
| WO | WO-96/04957 | 1/1995 |
| WO | WO-95/33514 | 12/1995 |
| WO | WO-96/11723 | 4/1996 |
| WO | WO-97/13550 | 4/1997 |
| WO | WO-97/49453 | 12/1997 |
| WO | WO-98/37926 | 9/1998 |
| WO | WO-98/43700 | 10/1998 |
| WO | WO-98/43701 | 10/1998 |
| WO | WO-98/48888 | 11/1998 |
| WO | WO-99/33407 | 7/1999 |
| WO | WO-99/51286 | 10/1999 |
| WO | WO-99/52424 | 10/1999 |
| WO | WO-01/26729 | 4/2001 |
| WO | WO-02/09808 | 2/2002 |
| WO | WO-02/26314 | 4/2002 |
| WO | WO-02/053207 | 7/2002 |
| WO | WO-02/070039 A2 | 9/2002 |
| WO | WO-02/070047 | 9/2002 |
| WO | WO 02/085448 | 10/2002 |
| WO | WO-03/018108 | 3/2003 |
| WO | WO-03/028802 | 4/2003 |
| WO | WO-03/063692 | 8/2003 |
| WO | WO-03/071140 A2 | 8/2003 |
| WO | WO-03/076008 | 9/2003 |
| WO | WO-03/082080 | 10/2003 |
| WO | WO-03/082403 | 10/2003 |
| WO | WO-2004/026370 | 4/2004 |
| WO | WO-2004/026371 | 4/2004 |
| WO | WO-2004/026374 | 4/2004 |
| WO | WO-2004/030718 | 4/2004 |
| WO | WO-2004/032791 | 4/2004 |
| WO | WO-2004/107965 | 12/2004 |
| WO | WO-2005014100 | 2/2005 |
| WO | WO-2005016165 | 2/2005 |
| WO | WO-2005/032646 A2 | 4/2005 |
| WO | WO-2005/065284 | 7/2005 |
| WO | WO-2005/084389 A2 | 9/2005 |
| WO | WO-2005/097256 A2 | 10/2005 |
| WO | WO-2005/123183 | 12/2005 |
| WO | WO-2006/007048 A2 | 1/2006 |
| WO | WO-2006018528 A1 | 2/2006 |

WO WO-2006/031899 A2 3/2006

OTHER PUBLICATIONS

Campese, V.M. et al., "Renal Afferent Denervation Prevents the Progression of Renal Disease in the Renal Ablation Model of Chronic Renal Failure in the Rat," American Journal of Kidney Diseases, vol. 26, No. 5, 1995, pp. 861-865.

DiBona, G.F. et al., "Interaction Between Renal Sympathetic Nerves and the Renin-Angiotensin System in the Control of Renal Function," Hypertension, 2000, 36:1083-1088.

DiBona, G.F., "Functionally Specific Renal Sympathetic Nerve Fibers: Role in Cardiovascular Regulation," American Journal of Hypertension, 2001, 14:163S-170S.

DiBona, G.F., "Sympathetic Nervous System and the Kidney in Hypertension," Current Opinion in Nephrology and Hypertension, 2002, 11:197-200.

Huang, Wann-Chu et al. "Renal Denervation Prevents and Reverses Hyperinsulinemia-Induced Hypertension in Rats," Hypertension, 1998, 32:249-254.

Nozawa, T. et al., "Effects of Long Term Renal Sympathetic Denervation on Heart Failure After Myocardial Infarction in Rats," Heart Vessels, 2002, 16:51-56.

Rump, L.C., "The Role of Sympathetic Nervous Activity in Chronic Renal Failure," J Clinical Basic Cardiology, 2001, 4:179.

U.S. Appl. No. 10/408,665, filed Apr. 8, 2003, Levin et al.
U.S. Appl. No. 11/129,765, filed May 13, 2005, Deem.
U.S. Appl. No. 11/133,925, filed May 20, 2005, Gelfand.
U.S. Appl. No. 11/144,298, filed Jun. 3, 2005, Levin et al.
U.S. Appl. No. 11/145,122, filed Jun. 3, 2005, Levin et al.
U.S. Appl. No. 11/189,563, filed Jul. 25, 2005, Deem.

Berde, C. et al. "Local Anesthetics," Anesthesia, Chapter 13, 5th addition, pp. 491-521, Churchill-Livingston, Philadelphia 2000.

Blad, B., et al., "An Electrical Impedance index to Assess Electroporation in Tissue," Tissue and Organ (Therapy), pp. 31-34, www.bl.uk <http://www.bl.uk> British Library, 2001, Oslo.

Braunwald, E., Heart Disease, "A Textbook of Cardiovascular Medicine," 5th Ed., vol. 2, 1997, pp. 480-481, 824-825, 1184-1288 and 1923-1925, W.B. Saunders Company.

Davalos, R. et al., "Electrical Impedance Tomography for Imaging Tissue Electroporation," IEEE Transactions on Biomedical Engineering, vol. 51, No. 5, May 2004, pp. 761-767, 2004 IEEE.

DiBona, G., "Neural Control of the Kidney: Functionally Specific Renal Sympathetic Nerve Fibers," Am J Physiol Regulatory Integrative Comp Physiol, 2000, 279: R1517-R1524, The American Physiological Society, Bethesda, MD.

Dueck, R. et al., "Noninvasive Cardiac Output Monitoring," The Cardiopulmonary and Critical Care Journal, Chest, 120, Aug. 2, 2001, pp. 339-341, American College of Chest Physicians.

Gehl, J. et al., "In Vivo Electroporation of Skeletal Muscle: Threshold, Efficacy and Relation to Electric Field Distribution," Biochimica et Biophysica Acta, 1428, 1999, pp. 233-240, www.elsevier.com/locate/bba_<http://www.elsevier.com/locate/bba>.

Hopp, F. A. et al., "Respiratory Responses to Selective Blockade of Carotid Sinus Baroreceptors in the Dog," Am J Physiol Regul Integr Comp Physiol, 1998, 275:10-18, American Physiological Society, Bethesda, MD.

International Search Report, PCT/US04/38498, Mailed Feb. 18, 2005, Applicant: G & L Consulting, LLC, 3 pgs.

Medrtonic Inc., MiniMed 2007, "Implantable Insulin Pump System" (Shoreview, MN) 4 pgs.

Miklavcic, D. et al, "A Validated Model of in Vivo Electric Field Distribution in Tissues for Electrochemotherapy and for DNA Electrotransfer for Gene Therapy," Biochimica et Biophysica Acta, 1523, 2000, pp. 73-83, www.elsevier.com/locate/bba<http://www.elsevier.com/locate/bba>.

Nelson, L. et al., "Neurogenic Control of Renal Function in Response to Graded Nonhypotensive Hemorrahage in Conscious Dogs," 1993, pp. R661-R667, American Physiological Society.

Cahana, A. et al., "Acute Differential Modulation of Synaptic Transmission and Cell Survival During Exposure to Pulsed and Continuous Radiofrequency Energy," The Journal of Pain, May 2003, pp. 197-202, vol. 4, No. 4, © 2003 by the American Pain Society.

Heida, T., et al., "Investigating Membrane Breakdown of Neuronal Cells Exposed to Nonuniform Electric Fields by Finite-Element Modeling and Experiments," IEEE Transactions on Biomedical Engineering, vol. 49, No. 10, Oct. 2002, pp. 1195-1203, © 2002 IEEE.

Lee, R. C., et al., "Biophysical Injury Mechanisms in Electrical Shock Trauma," Annu. Rev. Biomed. Eng., 2000. 02:477-509, Copyright © 2000 by Annual Reviews.

Podhajsky, R. J., et al. "The Histologic Effects of Pulsed and Continuous Radiofrequency Lesions at 42° C. to Rat Dorsal Root Ganglion and Sciatic Nerve," SPINE, vol. 30, No. 9, pp. 1008-1013, Lippincott Williams & Wilkins Inc.

U.S. Appl. No. 11/144,173, filed Jun. 3, 2005, Levin et al.
U.S. Appl. No. 11/233,814, Denise Demarais.
U.S. Appl. No. 11/252,462, Denise Demarais.
U.S. Appl. No. 11/266,993, Denise Demarais.
U.S. Appl. No. 11/324,188, Denise Demarais.
U.S. Appl. No. 11/363,867, Denise Demarais.
U.S. Appl. No. 11/368,553, Demarais.
U.S. Appl. No. 11/368,577, Demarais.
U.S. Appl. No. 11/368,809, Denise Demarais.
U.S. Appl. No. 11/368,836, Demarais.
U.S. Appl. No. 11/368,949, Denise Demarais.
U.S. Appl. No. 11/368,971, Denise Demarais.

"2003 European Society of Hypertension-European Society of Cardiology guidelines for the management of arterial hypertension," Journal of Hypertension 2003, vol. 21, No. 6, pp. 1011-1053.

"Advanced Neuromodulation Systems' Comparison Chart," 1 page.

"Advances in the role of the sympathetic nervous system in cardiovascular medicine," 2001 SNS Report, No. 3, Springer, published with an educational grant from Servier, pp. 1-8.

"Clinical Trials in Hypertension and Renal Diseases," Slide Source, www.hypertensiononline.org, 33 pages.

"ECM 830 Specifications Sheet," tech@genetronics.com, 20-001796-01 Rev D, 2 pages.

"Electrical Stimulation for the Treatment of Chronic Wounds," Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pages.

"Electropermeabilization (Electroporation)," Cyto Pulse Sciences Inc., http://www.cytopulse.com/electroporation.html (last accessed Mar. 3, 2005), 3 pages.

"Electroporation based Technologies and Treatments," ESPE Newsletter No. 6, QLK 02002-2003, Jan. 2005, www.cliniporator.com, 4 pages.

"End-stage renal disease payment policies in traditional Medicare," Report to the Congress: Medicare Payment Policy, Mar. 2001, Medpac, pp. 123-138.

"Epidemiology of Renal Disease in Hypertension," slide presentation by hypertensiononline.org, 21 pages.

"Fact Book Fiscal Year 2003," National Institutes of Health National Heart, Lung, and Blood Institute, Feb. 2004, 197 pages.

"Heart Disease and Stroke Statistics-2004 update," American Heart Association, American Stroke Association, Dallas, Texas, © 2003 American Heart Association, 52 pages.

"Hypertension and Renal Disease: Mechanisms," Slide Show by www.hypertensiononline.org, 22 pages.

"Hypertension Incidence and Prevalence, Age Specific Rates, by Gender, B.C., 2001/2002," Graph., Chronic Disease Management, May 2003, British Columbia Ministry of Health Services, 1 page.

"Infumedics Inc.," Background and products paper and comparison of Medtronic SynchroMed II and Infumedics Prometra pumps, 3 pages.

"Introduction to Autonomic Pharmacology," Chapter 3, Part 2 Autonomic Pharmacology, pp. 18-26.

"Market for infusion pumps grows with an aging population," NWL 97-01, The BBI Newsletter, vol. 20, No. 2, Feb. 1, 1997, American Health Consultants Inc., 6 pages.

"PHCL 762 Pharmacology of the Autonomic Nervous System," Chapter 2 and 6.8 in Mosby, http://www.kumc.edu/research/medicine/pharmacology/CAI/phc1762.html, last accessed Aug. 24, 2004, 14 pages.

"Programmable Infusion System," Pumps and Pump Selection, Medtronic Pain Therapies, Medtronic, Inc. Sep. 5, 2001, 2 pages.

"Pulmonary Concepts in Critical Care Breath Sounds," http://mbob.tripod.com/breath.htm, last accessed Aug. 23, 2004, 5 pages.

"Pulmonary Function Testing," http://jan.ucc.nau.edu/~daa/lecture/pft.htm, last accessed Aug. 23, 2004, 8 pages.

"Sensorcaine-MPF Spinal Injection," informational document, AstraZeneca 2001, 2 pages.

"Summary," Critical Reviews in Biomedical Engineering, vol. 17, Issue 5, 1989, pp. 515-529.

"The Antihypertensive and Lipid-Lowering Treatment to Prevent Heart Attack Trial," *Allhat Research Group*, JAMA 2002, vol. 288, pp. 2981-2997.

Aars, H. and S. Akre, "Reflex Changes in Sympathetic Activity and Arterial Blood Pressure Evoked by Afferent Stimulation of the Renal Nerve," Feb. 26, 1999, Acta Physiol. Scand., vol. 78, 1970, pp. 184-188.

Abramov, G.S. et al., "Alteration in sensory nerve function following electrical shock," Burns vol. 22, No. 8, © 1996 Elsevier Science Ltd., pp. 602-606.

Achar, Suraj, M.D. and Suriti Kundu, M.D., "Principles of Office Anesthesia: Part I. Infiltrative Anesthesia," Office Procedures, American Family Physician, Jul. 1, 2002, vol. 66, No. 1, pp. 91-94.

Agnew, William F. et al., "Evolution and Resolution of Stimulation-Induced Axonal Injury in Peripheral Nerve," May 21, 1999, Muscle and Nerve, vol. 22, Oct. 1999, © 1999 John Wiley & Sons, pp. 1393-1402.

Ahadian, Farshad M., M.D., "Pulsed Radiofrequency Neurotomy: Advances in Pain Medicine," Current Pain and Headache Reports 2004, vol. 8, © 2004 Current Science Inc., pp. 34-40.

Alford, J.Winslow, M.D. and Paul D. Fadale, M.D., "Evaluation of Postoperative Bupivacaine Infusion for Pain Management After Anterior Cruciate Ligament Reconstruction," The Journal of Arthroscopic and Related Surgery October, vol. 19, No. 8, © 2003 Arthroscopy Association of North American, pp. 855-861.

Andrews, B.T. et al., "The use of surgical sympathectomy in the treatment of chronic renal pain," Mar. 5, 1997, British Journal of Urology, vol. 80, © 1997 British Journal of Urology, pp. 6-10.

Archer, Steffan et al., "Cell Reactions to Dielectrophoretic Manipulation," Mar. 1, 1999, Biochemical and Biophysical Research Communications, 1999 Academic Press, pp. 687-698.

Arias, Manuel J., M.D., "Percutaneous Radio Frequency Thermocoagulation with Low Temperature in the Treatment of Essential Glossopharyngeal Neuralgia," Surg. Neurol. 1986, vol. 25, © 1986 Elsevier Science Publishing Co. Inc., pp. 94-96.

Aronofsky, David H., D.D.S., "Reduction of dental postsurgical symptoms using nonthermal pulsed high-peak-power electromagnetic energy," Oral Surg., Nov. 1971, vol. 32, No. 5, pp. 688-696.

Aspelin, Peter, M.D., Ph.D. et al, "Nephrotoxic Effects in High-Risk Patients Undergoing Angiography," Feb. 6, 2003, New England Journal of Medicine 2003, vol. 348, No. 6, 2003 Massachusetts Medical Society, pp. 491-499.

Awwad, Ziad M., FRCS and Bashir A. Atiyat, GBA, JBA, "Pain relief using continuous bupivacaine infusion in the paravertebral space after loin incision," May 15, 2004, Saudi Med. J. 2004, vol. 25, No. 10, pp. 1369-1373.

Badyal, D.K., H. Lata and A.P. Dadhich, "Animal Models of Hypertension and Effect of Drugs," Aug. 19, 2003, Indian Journal of Pharmacology 2003, vol. 35, pp. 349-362.

Baker, Carol E. et al., "Effect of pH of Bupivacaine on Duration of Repeated Sciatic Nerve Blocks in the Albino Rat," Anesth. Analg, 1991, vol. 72, © 1991 The International Anesthesia Research Society, pp. 773-778.

Balazs, Tibor, "Development of Tissue Resistance to Toxic Effects of Chemicals," Jan. 26, 1974, Toxicology, vol. 2, © 1974 Elsevier/North Holland, Amsterdam, pp. 247-255.

Barrett, Carolyn J. et al., "Long-term control of renal blood flow: what is the role of renal nerves?" Jan. 4, 2001, Am. J. Physiol. Regulatory Integrative Comp. Physiol. 2001, vol. 280, © 2001 the American Physiological Society, pp. R1534-R1545.

Barrett, Carolyn J. et al., "What Sets The Long-Term Level of Renal Sympathetic Nerve Activity?," May 12, 2003, Integrative Physiology, Circulation Research 2003, vol. 92, © 2003 American Heart Association, pp. 1330-1336.

Bassett, C. Andrew L. et al., "Augmentation of Bone Reapair by Inductively Coupled Electromagnetic Fields," May 3, 1974, Science, vol. 184, pp. 575-577.

Bassett, C. Andrew L., "Fundamental and Practical Aspects of Therapeutic Uses of Pulsed Electromagnetic Fields (PEMFs)," Critical Reviews in Biomedical Engineering, vol. 17, No. 5, 1989, pp. 451-514.

Beebe, Stephen J. et al., "Nanosecond Pulsed Electric Field (nsPEF) Effects on Cells and Tissues: Apoptosis Induction and Tumor Growth Inhibition," Oct. 11, 2001, IEEE Transactions on Plasma Science, vol. 30, No. 1, Feb. 2002, © 2002 IEEE, pp. 286-292.

Beebe, Stephen J. et al., "Nanosecond pulsed electric fields modulate cell function through intracellular signal transduction mechanisms," Apr. 8, 2004, Physiological Measurement, vol. 25, 2004, © 2004 IOP Publishing Ltd., pp. 1077-1093.

Bhadra, Niloy and Kevin L. Kilgore, "Direct Current Electrical Conduction Block of Peripheral Nerve," Feb. 25, 2004, IEEE Transactions on Neural Systems and Rehabilitation Engineering, vol. 12, No. 3, Sep. 2004, pp. 313-324.

Bhatt, Deepak L. et al., "Rhabdomyolysis Due to Pulsed Electric Fields," May 11, 1989, Plastic and Reconstructive Surgery Jul. 1990, pp. 1-11.

Bigler, D. et al., "Tachyphylaxis during postoperative epidural analgesia-new insights," Apr. 15, 1987, Letter to the Editor, Acta Anesthesiol. Scand. 1987, vol. 31, pp. 664-665.

Binder, Allan et al., "Pulsed Electromagnetic Field Therapy of Persistent Rotator Cuff Tendinitis," The Lancet, Saturday Mar. 31, 1984, The Lancet Ltd., pp. 695-698.

Black, Henry R., M.D., "Resistant Hypertension 2004," presentation at Rush University Medical Center, Jul. 15, 2004, 40 pages.

Blair, M.L. et al., "Sympathetic activation cannot fully account for increased plasma renin levels during water deprivation," Sep. 23, 1996, Am J Physiol 1997, vol. 272, © 1997 the American Physiological Society, pp. R1197-R1203.

Blomberg, Sture G., M.D., Ph.D., "Long-Term Home Self-Treatment with High Thoracic Epidural Anesthesia in Patients with Severe Coronary Artery Disease," Mar. 29, 1994, Anesth. Analg. 1994, vol. 79, © 1994 International Anesthesia Research Society, pp. 413-421.

Cahana, Alex, M.D., "Pulsed Radiofrequency: A Neurobiologic and Clinical Reality," May 17, 2005, Anesthesiology 2005, vol. 103, No. 6, Dec. 2005, © 2005 American Society of Anesthesiologists, Inc., Lippincott Williams & Wilkins, Inc., p. 1311.

Calaresu, F.R. et al., "Haemodynamic Responses and Renin Release During Stimulation of Afferent Renal Nerves in the Cat," Aug. 12, 1975, J. Physiol. 1976, vol. 255, pp. 687-700.

Campese, V.M., "A new model of neurogenic hypertension caused by renal injury: pathophysiology and therapeutic implications," Clin. Exp. Nephrol 2003, vol. 7, © 2003 Japanese Society of Nephroloogy, pp. 167-171.

Campese, V.M., "Neurogenic factors and hypertension in chronic renal failure," Journal of Nephrology, vol. 10, No. 4, © 1997 Societa Italiana di Nefrologia, pp. 184-187.

Carls, G., et at "Electrical and magnetic stimulation of the intercostal nerves: a comparative study," Electromyogr. clin. Neurophysiol., vol. 37, 1997, pp. 509-512.

Carlson, Scott H. and J. Michael Wyss, "e-Hyertension, Opening New Vistas," Introductory Commentary, Hypertension 2000, vol. 35, American Heart Association, Inc., 2000, p. 538.

Chang, Donald C., "Cell poration and cell fusion using an oscillating electric field," Biophysical Journal, vol. 56, Oct. 1989, Biophysical Society, pp. 641-652.

Chobanian, Aram V. et al., "Seventh Report of the Joint National Committee on Prevention, Detection, Evaluation, and Treatment of High Blood Pressure," Nov. 6, 2003, Hypertension 2003, vol. 42, © 2003 American Heart Association, Inc., pp. 1206-1252.

Codman 3000, Implantable Constant-Flow Infusion Pump Pamphlet, For Continuous Intrathecal Drug Delivery, 2 pages.

Conradi, E., Ines Helen Pages, "Effects of Continuous and Pulsed Microwave Irradiation on Distribution of Heat in the Gluteal Region of Minipigs," Scand. J. Rehab. Med., vol. 21, 1989, pp. 59-62.

Converse Jr., R.L. et al., "Sympathetic Overactivity in Patients with Chronic Renal Failure," New England Journal of Medicine, Dec. 31, 1992, vol. 327 (27), pp. 1912-1918.

Cosman, Eric R., Jr. et al., "Electric and Thermal Field Effects in Tissue Around Radiofrequency Electrodes," Pain Medicine, vol. 6, No. 6, 2005, American Academy of Pain Medicine, pp. 405-424.

Cosman, Eric R., Ph.D., "A Comment on the History of the Pulsed Radiofrequency Technique for Pain Therapy," Anesthesiology Dec. 2005, vol. 103, No. 6, © 2005 American Society of Anesthesiologists, Inc. Lippincott Williams & Wilkins, Inc., p. 1312.

Crawford, William H. et al., "Pulsed Radio Frequency Therapy of Experimentally Induced Arthritis in Ponies," Dec. 18, 1989, Can. J. Vet. Res. 1991, vol. 55, pp. 76-85.

Dahm, Peter et al., "Efficacy and Technical Complications of Long-Term Continuous Intraspinal Infusions of Opioid and/or Bupivacaine in Refractory Nonmalignant Pain . . . ," Oct. 6, 1997, The Clinical Journal of Pain 1998, vol. 14, No. 1, © 1998 Lippincott-Raven Publishers, pp. 4-16.

Dahm, Peter O. et al., "Long-Term Intrathecal Infusion of Opioid and/or Bupivacaine in the Prophylaxis and Treatment of Phantom Limb Pain," Neuromodulation 1998, vol. 1, No. 3, © 1998 International Neuromodulation Society, pp. 111-128.

Dang, Nicholas C. et al., "A Novel Approach to Increase Total Urine Output in Heart Failure: Renal Nerve Blockade," ACC 2005 poster, 1 page.

Davalos, R.V. et al., "Tissue Ablation with Irreversible Electroporation," Sep. 7, 2004, Annals of Biomedical Engineering, vol. 33, No. 2, © 2005 Biomedical Engineering Society, pp. 223-231.

De Leeuw, Peter W. et al., "Renal Vascular Tachyphylaxis to Angiotensin II: Specificity of the Response for Angiotensin," Dec. 28, 1981, Life Sciences, vol. 30, © 1982 Pergamon Press Ltd., pp. 813-819.

Deng, Jingdong et al., "The Effects of Intense Submicrosecond Electrical Pulses on Cells," Nov. 26, 2002, Biophysical Journal, vol. 84, Apr. 2003, © 2003 Biophysical Society, pp. 2709-2714.

Denton, Kate M. et al., "Differential Neural Control of Glomerular Ultrafiltration," Jan. 30, 2004, Proceedings of the Australian Physiological and Pharmacological Society Symposium: Hormonal, Metabolic and Neural Control of the Kidney, Clinical and Experimental Pharmacology and Physiology (2004), 31, pp. 380-386.

Dev, Nagendu B., Ph.D. et al., "Intravascular Electroporation Markedly Attenuates Neointima Formation After Balloon Injury of the Carotid Artery in the Rat," Journal of Interventional Cardiology, vol. 13, No. 5, 2000, pp. 331-338.

Dev, Nagendu B., Ph.D. et al., "Sustained Local Delivery of Heparin to the Rabbit Arterial Wall With an Electroporation Catheter," May 5, 1998, Catheterization and Cardiovascular Diagnosis 1998, vol. 45, © 1998 Wiley-Liss Inc., pp. 337-345.

DiBona, G., "Neural Control of the Kidney: Functionally Specific Renal Sympathetic Nerve Fibers," Starting Lecture, Am J Physiol Regulatory Integrative Comp Physiol 2000, 279, 2000 The American Physiological Society, pp. R1517-R1524.

Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R298-R305.

Dibona, Gerald F. and Ulla C. Kopp, "Role of the Renal Sympathetic Nerves in Pathophysiological States," Neural Control of Renal Function, vol. 77, pp. 142-197.

Dibona, Gerald F., "Neural Control of the Kidney-Past, Present, and Future," Nov. 4, 2002, Novartis Lecture, Hypertension 2003, vol. 41, part 2, © 2002 American Heart Association, pp. 621-624.

Dibona, Gerald F., "Peripheral and Central Interactions between the Renin-Angiotensin System and the Renal Sympathetic Nerves in Control of Renal Function," Annals New York Academy of Sciences, pp. 395-406.

Dibona, Gerald F., "Renal Innervation and Denervation: Lessons from Renal Transplantation Reconsidered," Artificial Organs, vol. 11, No. 6, Raven Press Ltd., © 1987 International Society for Artificial Organs, pp. 457-462.

Dibona, Gerald F., "The Sympathetic Nervous System and Hypertension," Dec. 4, 2003, Hypertension Highlights, Hypertension Feb. 2004, vol. 43, © 2004 American Heart Association, pp. 147-150.

Dibona, Gerald F., L.L. Sawin, "Effect of renal denervation on dynamic autoregulation of renal blood flow," Feb. 12, 2004, Am J Physiol Renal Physiol 286, pp. F1209-F1218.

Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.

Dorros, Gerald, M.D., "Renal Artery Stenting State of the Art," presentation, TCT, Washington D.C., Sep. 2003, 27 pages.

Dunn, Matthew D. et al., "Laparoscopic Nephrectomy in Patients With End-Stage Renal Disease and Autosomal Dominant Polycystic Kidney Disease," Oct. 25, 1999, American Journal of Kidney Diseases Apr. 2000, vol. 35, No. 4, © 2000 National Kidney Foundation, Inc., pp. 720-725.

Durand, D.M., "Electrical Field Effects in Hyperexcitable Neural Tissue: A Review," Radiation Protection Dosimetry, vol. 106, No. 4, 2003, Nuclear Technology Publishing, pp. 325-331.

Erdine, Serap and Alev Arat-Ozkan, "Resistant Hypertension," European Society of Hypertension Scientific Newsletter: Update on Hypertension Management, 2003, vol. 4, No, 15, 2 pages.

Fareed, Jawad, Ph.D. et al., "Some Objective Considerations for the Use of Heparins and Recombinant Hirudin in Percutaneous Transluminal Coronary Angioplasty," Seminars in Thrombosis and Hemostasis 1991, vol. 17, No. 4, © 1991 Thieme Medical Publishers, Inc., pp. 455-470.

Ferguson, D.R. et al., "Responses of the pig isolated renal artery to transmural electrical stimulation and drugs," Dec. 7, 1984, Br. J. Pharmac. 1985, vol. 84, © 1985 The Macmillan Press Ltd., pp. 879-882.

Fernandez-Ortiz, Antonio et al., "A New Approach for Local Intravascular Drug Delivery—Iontophoretic Balloon..," Intravascular Iontophoretic Local Delivery, Circulation, vol. 89, No. 4, Apr. 1994, pp. 1518-1522.

Fields, Larry E. et al, "The Burden of Adult Hypertension in the United States 1999 to 2000—A Rising Tide," May 18, 2004, © 2004 the American Heart Association, Hypertension Oct. 2004, pp. 1-7.

Freeman, Scott A. et al., "Theory of Electroporation of Planar Bilayer Membranes: Predictions of the Aqueous Area, Change in Capacitance, and Pore-Pore Separation," Feb. 23, 1994, Biophysical Journal, Jul. 1994, vol. 67, © 1994 by the Biophysical Society, pp. 42-56.

Fukuoka, Yuko et al., "Imaging of neural conduction block by neuromagnetic recording," Oct. 16, 2002, Clinical Neurophysiology 2002, vol. 113, © 2002 Elsevier Science Ireland Ltd., pp. 1985-1992.

Gami, Apoor S., M.D. and Vesna D. Garovic, M.D., "Contrast Nephropathy After Coronary Angiography," Mayo Clin Proc. 2004, vol. 79, 2004 Mayo Foundation for Medical Education and Research, pp. 211-219.

Gattone II, Vincent H. et al., "Contribution of Renal Innervation to Hypertension in Polycystic Kidney Disease in the Rat," University of Chicago Section of Urology, 16 pages.

Gaylor, D.C. et al., "Significance of Cell Size and Tissue Structure in Electrical Trauma," Jan. 26, 1998, J. Theor. Biol. 1988, vol. 133, © 1988 Academic Press Limited, pp. 223-237.

Ghoname, El-sayed A. et al., "Percutaneous electrical nerve stimulation: an alternative to TENS in the management of sciatica," Apr. 26, 1999, Pain 1999, vol. 83, © 1999 International Association for the Study of Pain / Published by Elsevier Science B.V., pp. 193-199.

Gimple, M.D., Lawrence et al., "Effect of Chronic Subcutaneous or Intramural Administration of Heparin on Femoral Artery Restenosis After Balloon Angioplasty in Hypercholesterolemic Rabbits" Laboratory Investigation, Circulation, vol. 86, No. 5, Nov. 1992, pp. 1536-1546.

Goldberger, Jeffrey J. et al., "New technique for vagal nerve stimulation," Jun. 2, 1999, Journal of Neuroscience Methods 91, © 1999 Elsevier Science B.V., pp. 109-114.

Gorbunov, F.E. et al., "The Use of Pulsed and Continuous Short Wave Diathermy (Electric Field) in Medical Rehabilitation of the Patients with Guillain-Barre Syndrome and Other Peripheral Myelinopathies," May 6, 1994, 5 pages (most of article in Russian language).

Greenwell, T.J. et al., "The outcome of renal denervation for managing loin pain haematuria syndrome," Oct. 30, 2003, Institute of Urology and Nephrology, London, UK, © 2004 BJU International, 4 pages.

Gruberg, Luis, M.D. et al., "The Prognostic Implications of Further Renal Function Deterioration Within 48 h of Interventional Coronary Procedures in Patients with Pre-existent Chronic Renal Insufficiency," Jun. 19, 2000, Journal of the American College of Cardiology 2000, vol. 36, No. 5, © 2000 by the American College of Cardiology, pp. 1542-1548.

Hajjar, Ihab, M.D., M.S. and Theodore A. Kotchen, M.D., "Trends in Prevalence, Awareness, Treatment, and Control of Hypertension in the United States, 1988-2000," JAMA, Jul. 9, 2003, vol. 290, No. 2, pp. 199-206.

Hamza, M.D., Mohamed A. et al., "Effect of the Duration of Electrical Stimulation on the Analgesic Response in Patients with Low Back Pain," Anesthesiology, vol. 91, No. 6, Dec. 1999, © 1999 American Society of Anesthesiologists, Inc., pp. 1622-1627.

Han, Hyo-Kyung and Gordon L. Amidon, "Targeted Prodrug Design to Optimize Drug Delivery," Mar. 21, 2000, AAPS Pharmsci. 2000, vol. 2, No. 1, article 6, pp. 1-11.

Higuchi, Yoshinori, M.D., Ph.D. et al., "Exposure of the Dorsal Root Ganglion in Rats to Pulsed Radiofrequency Currents Activates Dorsal Horn Lamina I and II Neurons," Dec. 4, 2001, Experimental Studies, Neurosurgery, vol. 50, No. 4, Apr. 2002, pp. 850-856.

Hildebrand, Keith R., D.V.M., Ph.D. et al., "Stability, Compatibility, and Safety of Intrathecal Bupivacaine Administered Chronically via an Implantable Delivery System," May 18, 2001, The Clinical Journal of Pain, vol. 17, No. 3, © 2001 Lippincott Williams & Wilkins Inc., pp. 239-244.

Hing, Esther, M.P.H. and Kimberly Middleton, B.S.N., M.P.H., "National Hospital Ambulatory Medical Care Survey: 2001 Outpatient Department Summary," Aug. 5, 2003, Advance Data From Vital and Health Statistics, No. 338, CDC, 32 pages.

Horwich, Tamara, M.D., "New Advances in the Diagnosis and Management of Acute Decompensated Heart Failure," the Heart.org Satellite program, CME Symposium presented on Nov. 8, 2004 at the Sheraton New Orleans Hotel, 4 pages.

Huang, Yifei et al., "Remodeling of the chronic severely failing ischemic sheep heart after coronary microembolization: functional, energetic, structural, and cellular responses," Jan. 8, 2004, Am J Physiol. 2004, vol. 286, © 2004 the American Physiological Society, pp. H2141-H2150.

Hughes, Gordon B., M.D. et al., "A Comparative Study of Neuropathologic Changes Following Pulsed and Direct Current Stimulation of the Mouse Sciatic Nerve," Jun. 27, 1980, American Journal of Otolaryngology, Nov. 1980, vol. 1, No. 5, pp. 378-384.

Israili, Z.H., "Clinical pharmacokinetics of angiotensin II (AT) receptor blockers in hypertension," Journal of Human Hypertension 2000, Macmillan Publishers Ltd., vol. 14, pp. S73-S86.

Janssen, Ben J.A. et al., "Effects of complete renal denervation and selective afferent renal denervation on the hypertension induced by intrarenal norepinephrine infusion on conscious rats," Jan. 4, 1989, Journal of Hypertension 1989, vol. 7, No. 6, © 1989 Current Science Ltd., pp. 447-455.

Johansson, Bjorn, "Electrical Membrane Breakdown, A Possible Mediator of the Actions of Electroconvulsive Therapy," Medical Hypotheses 1987, vol. 24, © 1987 Longman Group UK Ltd., pp. 313-324.

Jorgensen, William A. et al., "Electrochemical Therapy of Pelvic Pain: Effects of Pulsed Electromagnetic Fields (PEMF) on Tissue Trauma," Eur. J. Surg. 1994, vol. 160, Suppl. 574, © 1994 Scandinavian University Press, pp. 83-86.

Joshi, R.P. et al., "Improved energy model for membrane electroporation in biological cells subjected to electical pulses," Apr. 9, 2002, Physical Review E, vol. 65, 041920-1, © 2002 The American Physical Society, 8 pages.

Joshi, R.P. et al., "Self-consistent simulations of elctroporation dynamics in biological cells subjected to ultrashort electrical pulses," Jun. 21, 2001, Physical Review E, vol. 64, 011913, © 2001The American Physical Society, pp. 1-10.

Joshi, R.P., K.H. Schoenbach, "Mechanism for membrane electroporation irreversibility under high-intensity, ultrashort electrical pulse conditions," Nov. 11, 2002, Physical Review 2002, E 66, © 2002 The American Physical Society, pp. 052901-1-052901-4.

Kanduser, Masa et al, "Effect of surfactant polyoxyethylene glycol ($C_{12}E_8$) on electroporation of cell line DC3F," Aug. 20, 2002, Colloids and Surfaces A: Physiochem. Eng. Aspects 2003, vol. 214, © 2002 Elsevier Science B.V., pp. 205-217.

Katholi, Richard E., "Renal nerves in the pathogenesis of hypertension in experimental animals and humans," Am J Physiol., vol. 245, © 1983 the American Physiological Society, pp. F1-F14.

Kelleher, Catherine L. et al., "Characteristics of Hypertension in Young Adults With Autosomal Dominant Polycystic Kidney Disease Compared With the General U.S. Population," Jun. 9, 2004, American Journal of Hypertension 2004, pp. 1029-1034.

King, Ronald W.P., "Nerves in a Human Body Exposed to Low-Frequency Electromagnetic Fields," Jun. 7, 1999, IEEE Transactions on Biomedical Engineering Dec. 1999, vol. 46, No. 12, © 1999 IEEE, pp. 1426-1431.

Kinney, Brian M., M.D., "High-Tech Healing—The evolution of therapeutic electromagnetic fields in plastic surgery," Plastic Surgery Products, Jun. 2004, pp. 32-36, 3 pages.

Kok, R.J. et al., "Specific Delivery of Captopril to the Kidney with the Prodrug Captopril-Lysozyme," Aug. 16, 1998, The Journal of Pharmacology and Experimental Therapeutics, vol. 288, No. 1, © 1999 by the American Society for Pharmacology and Experimental Therapeutics, pp. 281-285.

Kon, Valentina, "Neural Control of Renal Circulation," Miner Electrolyte Metab 1989, vol. 15, © 1989 S. Karger AG, pp. 33-43.

Koyama, Shozo et al., "Relative Contribution of Renal Nerve and Adrenal Gland to Renal Vascular Tone During Prolonged Canine Hemorrhagic Hypotension," Sep. 24, 1992, Circulatory Shock 1993, vol. 39, © 1993 Wiley-Liss Inc., pp. 269-274.

Kozak, Lola Jean, Ph.D. et al., "National Hospital Discharge Survey: 2001 Annual Summary with Detailed Diagnosis and Procedure Data," Vital Health Statistics, Series 13, No. 156, Jun. 2004, CDC, 206 pages.

Lafayette, Richard A., M.D., "How Does Knocking Out Angiotensin II Activity Reduce Renal Injury in Mice?" Jun. 14, 1999, Journal Club, American Journal of Kidney Diseases, vol. 35, No. 1, Jan. 2000: © 2000 National Kidney Foundation Inc., pp. 166-172.

Lavie, Peretz, Ph.D. and Victor Hoffstein, M.D., "Sleep Apnea Syndrome: A Possible Contributing Factor to Resistant Hypertension," Jun. 2001, Sleep 2001, vol. 24, No. 6, pp. 721-725.

Lee, Raphael C. and Jurgen Hannig, "Membrane Biology and Biophysics," Chapter 25, Surgical Research, © 2001 Academic Press, pp. 297-305.

Lee, Raphael C. et al., "Clinical Sequelae Manifested in Electrical Shock Survivors," Presentation by the Electrical Trauma Research Program, The University of Chicago, 37 pages.

Lee, Raphael C., M.D., Sc.D. and Michael S. Kolodney, S.B., "Electrical Injury Mechanisms: Electrical Breakdown of Cell Membranes," Oct. 1, 1986, Plastic and Reconstructive Surgery Nov. 1987, vol. 80, No. 5, pp. 672-679.

Ligtenberg, Gerry, M.D. et al., "Reduction of Sympathetic Hyperactivity by Enalapril in Patients with Chronic Renal Failure," Apr. 29, 1999, New England Journal of Medicine 1999, vol. 340, No. 17, © 1999 Massachusetts Medical Society, pp. 1321-1328.

Lin, Vernon W. H. et al, "High intensity magnetic stimulation over the lumbosacral spine evokes antinociception in rats," Apr. 16, 2002, Clinical Neurophysiology, vol. 113, © 2002 Elsevier Science Ireland Ltd., pp. 1006-1012.

Lipfert, Peter, M.D. et al., "Tachyphylaxis to Local Anesthetics Does Not Result From Reduced Drug Effectiveness at the Nerve Itself," Aug. 3, 1988, Anesthesiology 1989, vol. 70, pp. 71-75.

Lohmeier Thomas E. et al, "Baroreflexes prevent neurally induced sodium retention in angiotensin hypertension," Am. J. Physiol. Regulatory Integrative Comp. Physiol., vol. 279, © 2000 the American Physiological Society, pp. R1437-R1448.

Lohmeier, Thomas E. and Drew A. Hildebrandt, "Renal Nerves Promote Sodium Excretion in Angiotensin-Induced Hypertension," Oct. 20, 1997, Hypertension 1998, vol. 31, Part 2, © 1998 American Heart Association, Inc., pp. 429-434.

Lohmeier, Thomas E. et al., "Prolonged Activation of the Baroflex Produces Sustained Hypotension," Harry Goldblatt Award, Nov. 26, 2003, Hypertension 2004, vol. 43, part 2, © 2004 American Heart Association, Inc., pp. 306-311.

Lohmeier, Thomas E. et al., "Renal Nerves Promote Sodium Excretion During Long-Term Increases in Salt Intake," Oct. 23, 1998, Hypertension 1999, vol. 33, part 2, © 1999 American Heart Association, pp. 487-492.

Lohmeier, Thomas E. et al., "Sustained influence of the renal nerves to attenuate sodium retention in angiotensin hypertension," Apr. 13, 2001, Am J Physiol Regulatory Integrative Comp. Physiol., vol. 281, © 2001 the American Physiological Society, pp. R434-R443.

Lohmeier, Thomas E., "Interactions Between Angiotensin II and Baroreflexes in Long-Term Regulation of Renal Sympathetic Nerve Activity," Circulation Research, Jun. 27, 2003, © 2003 American Heart Association Inc., pp. 1282-1284.

Luff, S.E. et al., "Two types of sympathetic axon innervating the juxtaglomerular arterioles of the rabbit and rat kidney differ structurally from those supplying other arteries," May 1, 1991, Journal of Neurocytology 1991, vol. 20, © 1991 Chapman and Hall Ltd., pp. 781-795.

Lundborg, C. et al., "Clinical experience using intrathecal (IT) bupivacaine infusion in three patients with complex regional pain syndrome type I (CRPS-I)," Acta Aneaesthesiol. Scand. 1999, vol. 43, pp. 667-678.

Macarthur, Dr. Alison, "Spinal Anesthesia and Severe Gestational Hypertension," presentation at Mount Sinai Hospital, 25 pages.

Maeder, Micha, M.D. et al., "Contrast Nephropathy: Review Focusing on Prevention," Jun. 22, 2004, Journal of the American College of Cardiology Nov. 2, 2004, vol. 44, No. 9, © 2004 by the American College of Cardiology Foundation, pp. 1763-1771.

Malpas, Simon C., "What sets the long-term level of sympathetic nerve activity: is there a role for arterial baroreceptors?" Invited Review, Am J Physiol Regul. Integr. Comp. Physiol. 2004, vol. 286, © 2004 the American Physiological Society, pp. R1-R12.

Marenzi, Giancarlo, M.D. et al., "The Prevention of Radiocontrast-Agent-Induced Nephropathy by Hemofiltration," New England Journal of Medicine, Oct. 2, 2003, vol. 349 (14), © 2003 Massachusetts Medical Society, pp. 1333-1340.

Martin, Jason B. et al., "Gene Transfer to Intact Mesenteric Arteries by Electroporation," Mar. 27, 2000, Journal of Vascular Research 2000, vol. 37, 2000 S. Karger AG, Basel, pp. 372-380.

McCreery, Douglas B. et al., "Charge Density and Charge Per Phase as Cofactors in Neural Injury Induced by Electrical Stimulation," IEEE Transactions on Biomedical Engineering, vol. 17, No. 10, Oct. 1990, pp. 996-1000.

McCullough, Peter A., M.D., MPh et al., "Acute Renal Failure after Coronary Intervention: Incidence, Risk Factors and Relationship to Mortality," Apr. 14, 1997, Am J Med. 1997, vol. 103, 1997 Excerpta Medica, Inc., pp. 368-375.

McMurray, John J.V., M.D. and Eileen O'Meara, M.D., "Treatment of Heart Failure with Spironolactone-Trial and Tribulations," Aug. 5, 2004, New England Journal of Medicine, vol. 351, No. 6, © 2004 Massachusetts Medical Society, pp. 526-528.

McRobbie, D. and M.A. Foster, "Thresholds for biological effects of time-varying magnetic fields," Dec. 16, 1983, Clin. Phys. Physiol. Meas. 1984, vol. 5, No. 2, © 1984, The Institute of Physics, pp. 67-78.

Medtronic Neurostimulation Systems, "Expanding the Array of Pain Control Solutions," informational pamphlet, 1999 Medtronic, Inc., 6 pages.

Medtronic, "Spinal Cord Stimulation," Patient Management Guidelines for Clinicians, Medtronic, Inc. 1999, 115 pages.

Medtronic, "SynchroMed Infusion System—Clinical Reference Guide for Pain Therapy," Medtronic, Inc. 1998, 198 pages.

Mess, Sarah A., M.D. et al., "Implantable Baclofen Pump as an Adjuvent in Treatment of Pressure Sores," Mar. 1, 2003, Annals of Plastic Surgery, vol. 51, No. 5, Nov. 2003, © 2003 Lippincott Williams & Wilkins, pp. 465-467.

Mihran, Richard T. et al., "Temporally-Specific Modification of Myelinated Axon Excitability in Vitro Following A Single Ultrasound Pulse," Sep. 25, 1989, Ultrasound in Med.& Biol. 1990, vol. 16, No. 3, pp. 297-309.

Mitchell, G.A.G., "The Nerve Supply of the Kidneys," Aug. 20, 1949, Acta Anatomica, vol. 10, Fasc. 1/2, 1950, pp. 1-37.

Moss, Nicholas G., "Renal function and renal afferent and efferent nerve activity," Am J Physiol 1982, vol. 243, © 1982, the American Physiological Society, pp. F425-F433.

Munglani, Rajesh, "The longer term effect of pulsed radiofrequency for neuropathic pain," Jun. 8, 1998, Pain, vol. 80, © 1999 International Association for the Study of Pain, Published by Elsevier Science B.V., pp. 437-439.

Naropin (ropivacaine HCI) injection, Rx only description, AstraZeneca 2001, 3 pages.

National High Blood Pressure Education Program, "1995 Update of the Working Group Reports on Chronic Renal Failure and Renovascular Hypertension," presentation, 13 pages.

National Kidney Foundation, "Are You At Increased Risk for Chronic Kidney Disease?" © 2002 National Kidney Foundation, Inc., 14 pages.

Nikolsky, Eugenia, M.D. et al., "Radiocontrast Nephropathy: Identifying the High-Risk Patient and the Implications of Exacerbating Renal Function," Rev Cardiovasc Med. 2003, vol. 4, Supp. 1, © 2003 MedReviews, LLC, pp. S7-S14.

Palmer, Biff F., M.D., "Managing Hyperkalemia Caused by Inhibitors of the Renin-Angiotensin-Aldosterone System," Aug. 5, 2004, The New England Journal of Medicine 2004, vol. 351, No. 6, © 2004 Massachusetts Medical Society, pp. 585-592.

Peacock, J.M. and R. Orchardson, "Action potential conduction block of nerves in vitro by potassium citrate, potassium tartrate and potassium oxalate," May 6, 1998, Journal of Clinical Periodontology, © 1999 Munksgaard, vol. 26, pp. 33-37.

Pettersson, A. et al., "Renal interaction between sympathetic activity and ANP in rats with chronic ischaemic heart failure," Nov. 25, 1998, Acta Physiol. Scand. 1989, vol. 135, pp. 487-492.

Pliquett, U., "Joule heating during solid tissue electroporation," Oct. 22, 2002, Medical & Biological Engineering and Computing 2003, vol. 41, pp. 215-219.

Popovic, Jennifer .R. and Margaret J. Hall,"1999 National Hospital Discharge Survey," Advance Data, No. 319, CDC, pp. 1-17 & 20.

Practice Guidelines Writing Committee and ESH/ESC Hypertension Guidelines Committee, "Practice Guidelines For Primary Care Physicians: 2003 ESH/ESC Hypertension Guidelines," Published in Journal of Hypertension 2003, vol. 21, No. 10: 1011-1053, © 2003 European Society of Hypertension, pp. 1779-1786.

Pucihar, Gorazd et al., "The influence of medium conductivity on electropermeabilization and survival of cells in vitro," May 31, 2001, Bioelectrochemistry, vol. 54, 2001, Elsevier Science B.V. 2001, pp. 107-115.

Raji, A. R. M. and R. E. M. Bowden, "Effects of High-Peak Pulsed Electromagnetic Field on the Degeneration and Regeneration of the Common Peroneal Nerve in Rats," The Journal of Bone and Joint Surgery Aug. 1983, vol. 65-B, No. 4, © 1983 British Editorial Society of Bone and Joint Surgery, pp. 478-492.

Ram, C. Venkata S., M.D., "Understanding refractory hypertension," May 15, 2004, Patient Care May 2004, vol. 38, pp. 12-16, 7 pages from http://www.patientcareonline.com/patcare/content/printContentPopup.jsp?id=108324.

Ravalia, A. et al., "Tachyphylaxis and epidural anesthesia," Edgware General Hospital, Correspondence, p. 529.

Ribstein, Jean and Michael H. Humphreys, "Renal nerves and cation excretion after acute reduction in functioning renal mass in the rat," Sep. 22, 1983, Am J Physiol, vol. 246, © 1984 the American Physiological Society, pp. F260-F265.

Richebe, Philippe, M.D. et al., "Immediate Early Genes after Pulsed Radiofrequency Treatment: Neurobiology in Need of Clinical Trials," Oct. 13, 2004, Anesthesiology Jan. 2005, vol. 102, No. 1, © 2004 American Society of Anesthesiologists, Inc. Lippincott Williams & Wilkins, Inc., pp. 1-3.

Rihal, Charanjit S. et al., "Incidence and Prognostic Importance of Acute Renal Failure After Percutaneous Coronary Intervention," Mar. 6, 2002, Circulation May 14, 2002, vol. 10, © 2002 American Heart Association, Inc., pp. 2259-2264.

Rosen, S.M. et al., "Relationship of Vascular Reactivity to Plasma Renin Concentration in Patients with Terminal Renal Failure," Proc. Dialysis Transplant Forum 1974, pp. 45-47.

Roth, Bradley J. and Peter J. Basser, "A Model of the Stimulation of a Nerve Fiber by Electromagnetic Induction," IEEE Transactions on Biomedical Engineering, vol. 37, No. 6, Jun. 1990, pp. 588-597.

Rudin, Asa, M.D. et al., "Postoperative Epidural or Intravenous Analgesia after Major Abdominal or Thoraco-Abdominal Surgery," The Journal of the American Society of Anesthesiologists, Inc., Anesthesiology 2001, vol. 95, A-970, 1 page.

Rudnick, Michael R. et al., "Contrast-induced nephropathy: How it develops, how to prevent it," Cleveland Clinic Journal of Medicine Jan. 2006, vol. 73, No. 1, pp. 75-87.

Ruohonen, Jarmo et al., "Modeling Peripheral Nerve Stimulation Using Magnetic Fields," Journal of the Peripheral Nervous System 1997, vol. 2, No. 1, © 1997 Woodland Publications, pp. 17-29.

Scheiner, Avram, Ph.D., "The design, development and implementation of electrodes used for functional electrical stimulation," Thesis paper, Case Western Reserve University, May 1992, 220 pages.

Schoenbach, Kari H. et al., "Intracellular Effect of Ultrashort Electrical Pulses," Dec. 26, 2000, Bioelectromagnetics 2001, vol. 22, © 2001 Wiley-Liss Inc., pp. 440-448.

Schrier, Robert et al., "Cardiac and Renal Effects of Standard Versus Rigorous Blood Pressure Control in Autosomal-Dominant Polycystic Kidney Disease," Mar. 23, 2002, Journal of the American Society of Nephrology, © 2002 American Society of Nephrology, pp. 1733-1739.

Scremin, Oscar U., M.D., Ph.D. and Danel P. Holschneider, M.D., "31. & 32. An Implantable Bolus Infusion Pump for the Neurosciences," FRP, Apr. 2005, 3 pages.

Shu-Qing, Liu et al., "Old spinal cord injury treated by pulsed electric stimulation," General Hospital of Beijing Command, Beijing, 5 pages (full article in Chinese; abstract on last page).

Shupak, Naomi M., "Therapeutic Uses of Pulsed Magnetic-Field Exposure: A Review," Radio Science Bulletin Dec. 2003, No. 307, pp. 9-32.

Simpson, B. et al, "Implantable Spinal Infusion Devices for Chronic Pain and Spasticity: An Accelerated Systematic Review," ASERNIP-S Report No. 42, May 2003, 56 pages.

Sisken, B.F. et al., "229.17 Influence of Non-Thermal Pulsed Radiofrequency Fields (PRF) on Neurite Outgrowth," Society for Neuroscience, vol. 21, 1995, 2 pages.

Skeie, B. et al., "Effect of chronic bupivacaine infusion on seizure threshold to bupivacaine," Dec. 28, 1986, Acta Anaesthesiol. Scand. 1987, vol. 31, pp. 423-425.

Skopec, M. "A Primer on Medical Device Interactions with Magnetic Resonance Imaging Systems," Feb. 4, 1997, CDRH Magnetic Resonance Working Group, U.S. Department of Health and Human Services, Food and Drug Administration, Center for Devices and Radiological Health, Updated May 23, 1997, 17 pages, http://www.fde.gov/cdrh/ode/primerf6.html, (last accessed Jan. 23, 2006).

Slappendel, Robert et al., "The efficacy of radiofrequency lesioning of the cervical spinal dorsal root ganglion in a double blinded randomized study," Jun. 26, 1997, Pain, vol. 73, © 1997 International Association of the Study of Pain, Elsevier Science B.V., pp. 159-163.

Sluijter, M.D., Ph.D., "Pulsed Radiofrequency," May 17, 2005, Anesthesiology Dec. 2005, vol. 103, No. 6, © 2005 American Society of Anesthesiologists, Inc. Lippincott Williams & Wilkins, Inc., pp. 1313-1314.

Sluijter, M.D., Ph.D., "Radiofrequency Part 1: The Lumbosacral Region," Chapter 1 Mechanisms of Chronic Pain and part of Chapter 2 Spinal Pain, © 2001 FlivoPress SA, Meggen (LU), Switzerland, pp. 1-26.

Sluijter, M.D., Ph.D., "Radiofrequency Part 2: Thoracic and Cervical Region, Headache and Facial Pain," various pages from, FlivoPress SA, Meggen (LU), Switzerland, 13 pages.

Sluijter, M.D., Ph.D., "The Role of Radiofrequency in Failed Back Surgery Patients," Current Review of Pain 2000, vol. 4, © 2000 by Current Science Inc., pp. 49-53.

Souza, D.R.B. et al., "Chronic experimental myocardial infarction produces antinatriuresis by a renal nerve-dependent mechanism," Oct. 14, 2003, Brazilian Journal of Medical and Biological Research 2004, vol. 37, pp. 285-293.

Standl, Thomas, M.D., et al, "Patient-controlled epidural analgesia reduces analgesic requirements compared to continuous epidural infusion after major abdominal surgery," Aug. 29, 2002, Canada Journal of Anesthesia 2003, vol. 50, No. 3, pp. 258-264.

Stone, Gregg W., M.D. et al., "Fenoldopam Mesylate for the Prevention of Contrast-Induced Nephropathy," JAMA Nov. 5, 2003, vol. 290, No. 17, © 2003 American Medical Association, pp. 2284-2291.

Sung, Duk Hyun, M.D. et al., "Phenol Block of Peripheral Nerve Conduction: Titrating for Optimum Effect," Jun. 27, 2000, Arch. Phys. Med. Rehabil., vol. 82, May 2001, pp. 671-676.

Taler, Sandra J. et al., "Resistant Hypertension, Comparing Hemodynamic Management to Specialist Care," Mar. 12, 2002, Hypertension 2002, vol. 39, 2002 American Heart Association, Inc., pp. 982-988.

Tay, Victoria KM et al., "Computed tomography fluoroscopy-guided chemical lumbar sympathectomy: Simple, safe and effective," Oct. 31, 2001, Diagnositc Radiology, Australasian Radiology 2002, vol. 46, pp. 163-166.

Thompson, Gregory W. et al, "Bradycardia Induced by Intravascular Versus Direct Stimulation of the Vagus Nerve," Aug. 24, 1997, The Society of Thoracic Surgeons 1998, pp. 637-642.

Thrasher, Terry N., "Unloading arterial baroreceptors causes neurogenic hypertension," Dec. 4, 2001, Am J Physiol Regulatory Integrative Comp. Physiol., vol. 282, © 2002 the American Physiological Society, pp. R1044-R1053.

Tokuno, Hajime A. et al., "Local anesthetic effects of cocaethylene and isopropylcocaine on rat peripheral nerves," Oct. 7, 2003, Brain Research 996, 2004, © 2003 Elsevier B.V., pp. 159-167.

Trapani, Angelo J. et al., "Neurohumoral interactions in conscious dehydrated rabbit," Am J Physiol 1988, vol. 254, © 1988 the American Physiological Society, pp. R338-R347.

Trock, David H. et al., "The Effect of Pulsed Electromagnetic Fields in the Treatment of Osteoarthritis of the Knee and Cervical Spine. Report of Randomized, Double Blind, Placebo Controlled Trials," Mar. 22, 1994, The Journal of Rheumatology 1994, vol. 21, pp. 1903-1911.

Troiano, Gregory C. et al., "The Reduction in Electroporation Voltages by the Addition of a Surfactant to Planar Lipid Bilayers," May 12, 1998, Biophysical Journal, vol. 75, Aug. 1998, © the Biophysical Society, pp. 880-888.

Trumble, Dennis R., and James A. Magovern, "Comparison of Dog and Pig Models for Testing Substernal Cardiac Compression Devices," Nov. 2003, ASAIO Journal 2004, pp. 188-192.

Tsai, E., "Intrathecal drug delivery for pain indications, technique, results," Pain Lecture presentation, Jun. 8, 2001, 31 pages.

Uematsu, Toshihiko, M.D., Ph.D., F.I.C.A. et al., "Extrinsic Innervation of the Canine Superior Vena Cava, Pulmonary, Portal and Renal Veins," Angiology-Journal of Vascular Diseases, Aug. 1984, pp. 486-493.

United States Renal Data System, "USRDS 2003 Annual Data Report: Atlas of End-Stage Renal Disease in the United States," National Institutes of Health, National Institute of Diabetes and Digestive and Kidney Diseases, 2003, 593 pages.

Upadhyay, Pramod, "Electroporation of the skin to deliver antigen by using a piezo ceramic gas igniter," Jan. 27, 2001, International Journal of Pharmaceutics, vol. 217, © 2001 Elsevier Science B.V., pp. 249-253.

Valente, John F. et al., "Laparoscopic renal denervation for intractable ADPKD-related pain," Aug. 24, 2000, Nephrology Dialysis Transplantation 2001, vol. 16, European Renal Association-European Dialysis and Transplant Association, p. 160.

Van Antwerp, Bill and Poonam Gulati., "Protein Delivery from Mechanical Devices Challenges and Opportunities," Medtronic Presentation, 19 pages.

Velazquez, Eric J., "An international perspective on heart failure and left ventricular systolic dysfunction complicating myocardial infarction: the VALIANT registry," Aug. 5, 2004, European Heart Journal, vol. 25, © 2004 Elsevier Ltd., pp. 1911-1919.

Velez-Roa, Sonia, M.D., et al., "Peripheral Sympathetic Control During Dobutamine Infusion: Effects of Aging and Heart Failure," Jul. 7, 2003, Journal of the American College of Cardiology 2003, vol. 42, No. 9, © 2003 American College of Cardiology Foundation, pp. 1605-1610.

Vigilance, Deon W. et al., "A Novel Approach to Increase Total Urine Output in Acute Heart Failure: Unilateral Renal nerve Blockade," RNB Abstract AHA, 2 pages.

Villarreal, Daniel et al., "Effects of renal denervation on postprandial sodium excretion in experimental heart failure," Oct. 29, 1993, Am J Physiol 266, 1994, pp. R1599-R1604.

Villarreal, Daniel et al., "Neurohumoral modulators and sodium balance in experimental heart failure," Nov. 6, 1992, Am J Physiol, vol. 264, 1993, pp. H1187-H1193.

Wagner, C.D. et al, "Very low frequency oscillations in arterial blood pressure after autonomic blockade in conscious dogs," Feb. 5, 1997, Am J Physiol Regul Integr Comp Physiol 1997, vol. 272, © 1997 the American Physiological Society, pp. 2034-2039.

Wald, Jan D. Ph.D. et al., "Cardiology Update 2003," Sep. 11, 2003, © 2003 AG Edwards, 120 pages.

Wang, Xi et al., "Alterations of adenylyl cyclase and G proteins in aortocaval shut-induced heart failure," Jul. 2004, Am J Physiol Heart Circ Physiol., vol. 287, © 2004 the American Physiological Society, pp. H118-H125.

Weaver, James C., "Chapter 1: Electroporation Theory, Concepts and Mechanisms," Methods in Molecular Biology, vol. 55, Plant Cell Electroporation and Electrofusion Protocols, Edited by J.A. Nickoloff, © Humana Press Inc., pp. 3-28.

Weaver, James C., "Electroporation: A General Phenomenon for Manipulating Cells and Tissues," Oct. 22, 1992, Journal of Cellular Biochemistry, vol. 51, © 1993 Wiley-Liss, Inc., pp. 426-435.

Weiner, Richard L., M.D., "Peripheral nerve neurostimulation," Neurosurgery Clinics of North America 2003, vol. 14, © 2003 Elsevier Inc., pp. 401-408.

Weisbord, Steven D., M.D. and Paul M. Palevsky, M.D., "Radiocontrast-Induced Acute Renal Failure," Jul. 10, 2004, Journal of Intensive Care Medicine 2005, vol. 20 (2), © 2005 Sage Publications, pp. 63-75.

Wilson, D.H. et al., "The Effects of Pulsed Electromagnetic Energy on Peripheral Nerve Regeneration," Annals New York Academy of Sciences, pp. 575-585.

Wolinsky, Harvey, M.D., Ph.D. and Swan N. Thung, M.D., "Use of a Perforated Balloon Catheter to Deliver Concentrated Heparin Into the Wall of the Normal Canine Artery," Aug. 30, 1989, JACC 1990, vol. 15, © 1990 The American College of Cardiology, pp. 475-481.

Wyss, J.Michael et al., "Neuronal control of the kidney: Contribution to hypertension," Apr. 8, 1991, Can. J. Physiol. Pharmacol., vol. 70, 1992, pp. 759-770.

Yamaguchi, Jun-ichi et al., "Prognostic Significance of Serum Creatinine Concentration for In-Hospital Mortality in Patients With Acute Myocardial Infarction Who Underwent Successful Primary Percutaneous Coronary Intervention (from the Heart Institute of Japan Acute Myocardial Infarction [HIJAMI] Registry)," Feb. 24, 2004, The American Journal of Cardiology, vol. 93, Jun. 15, 2004, © 2004 by Excerpta Medica, Inc., pp. 1526-1528.

Ye, Richard D., M.D., Ph.D., "Pharmacology of the Peripheral Nervous System," E-425 MSB, 6 pages.

Ye, Shaohua et al., "Renal Injury Caused by Intrarenal Injection of Phenol Increases Afferent and Efferent Renal Sympathetic Nerve Activity," Mar. 12, 2002, American Journal of Hypertension Aug. 2002, vol. 15, No. 8, © 2002 the American Journal of Hypertension, Ltd. Published by Elsevier Science Inc., pp. 717-724.

Yong-Quan, Dong et al., "The therapeutic effect of pulsed electric field on experimental spinal cord injury," Beijing Army General Hospital of People's Liberation Army, Beijing, 5 pages (full article in Chinese; abstract on last page).

Young, James B., M.D., Facc, "Management of Chronic Heart Failure: What Do Recent Clinical Trials Teach Us?" Reviews in Cardiovascular Medicine 2004, vol. 5, Suppl. 1, © 2004 MedReviews, LLC, pp. S3-S9.

Zanchetti, A. et al., "Neural Control of the Kidney—Are There Reno-Renal Reflexes?" Clin. and Exper. Hyper. Theory and Practice, A6 (1&2), © 1984 Marcel Dekker Inc., pp. 275-286.

Zimmermann, Ulrich, "Electrical Breakdown, Electropermeabilization and Electrofusion," Rev. Physiol. Biochem. Pharmacol., vol. 105, © Springer-Verlag 1986, pp. 175-256.

Zucker, Irving H. et al., "The origin of sympathetic outflow in heart failure: the roles of angiotensin II and nitric oxide," Progress in Biophysics & Molecular Biology 2004, vol. 84, © 2003 Elsevier Ltd., pp. 217-232.

Zundert, Jan Van, M.D. Fipp and Alex Cahana, M.D. Daapm, "Pulsed Radiofrequency in Chronic Pain Management: Looking for the Best Use of Electrical Current," Pain Practice 2005, vol. 5, Issue 2, © 2005 World Institute of Pain, pp. 74-76.

Cameron, Tracy. "Micromodular Implants to Provide Electrical Stimulation of Paralyzed Muslces and Limbs." IEEE Transactions on Biomedical Engineering, vol. 44, No. 9, Sep. 1997. pp. 781-790.

Guimaraes, Sarfim. "Vascular Adrenoceptors: An Update" pp. 319-356.

Hammer, Leah W. "Differential Inhibition of Functional Dilation of Small Arterioles by Indomethacin and Glibenclamide." Hypertension. Feb. 2001 Part II. pp. 599-603.

Hortobagyi, Gabriel N. "Randomized Trial of High-Dose Chemotherapy and Blood Cell Autografts for High-Risk Primary Breast Carcinoma" Journal of the National Cancer Institute, vol. 92, No. 3, Feb. 2, 2000 pp. 225-233.

Janda, J., "Impact of the electrical stimulation apparatus rebox on the course of ischemic renal damage in rats," British Library-"The world's knowledge" pp. 252-254 (translated and untranslated versions).

U.S. Appl. No. 11/504,117, Demarais et al.
U.S. Appl. No. 11/599,649, Demarais et al.
U.S. Appl. No. 11/599,723, Demarais et al.
U.S. Appl. No. 11/599,882, Demarais et al.
U.S. Appl. No. 11/599,890, Demarais et al.
U.S. Appl. No. 11/688,178, Levin et al.

Alexander, B.T. et al., Renal denervation abolishes hypertension in low-birth-weight offspring from pregnant rats with reduced uterine perfusion, Hypertension, 2005; 45 (part 2): 754-758.

O'Hagan, K.P. et al., "Renal denervation decreases blood pressure in DOCA-treated miniature swine with established hypertension," AJH, 1990, 3:62-64.

Kassab, S. et al., "Renal denervation attenuates the sodium retention and hypertension associated with obesity," Hypertension, 1995, 25:893-897.

Zanchetti, A.S., "Neural regulation of renin release: Experimental evidence and clinical implications in arterial hypertension," Circulation, 1977, 56(5) 691-698.

Bell-Reuss, E. et al., "Effect of renal sympathetic nerve stimulation on proximal sodium reabsorption," J Clin Invest, 1976, 57(4) 1104-1107.

Kirchheim, H. et al., "Sympathetic modulation of renal hemodynamics, renin release and sodium excretion," Klin Wochenschr, 1989, 67:858-864.

Esler, M. et al., "Sympathetic nerve biology in essential hypertension," Clin and Exp Pharmacology and Physiology, 2001, 28: 986-989.

Schlaich M.P. et al., "Sympathetic augmentation in hypertension: role of nerve firing, norepinephrine reuptake, and angiotensin neuromodulation," Hypertension, 2004, 43:169-75.

Katholi, R.E., "Renal nerves and hypertension: an update," Fed Proc., 1985, 44: 2846-2850.

Katholi, R.E. et al., "Importance of the renal nerves in established two-kidney, one clip Goldblatt hypertension," Hypertension, 1982, 4 (suppl II): 11-166-11-174.

Katholi, R.E. et al., "Role of the renal nerves in the pathogenesis of one-kidney renal hypertension in the rat," Hypertension, 1981, 3(4) 404-409.

Kopp, U. et al., "Dietary sodium loading increases arterial pressure in afferent renal-denervated rats," Hypertension, 2003, 42:968-973.

Hausberg, M. et al., "Sympathetic nerve activity in end-stage renal disease," Circulation, 2002, 106: 1974-1979.

Luippold, G. et al., "Chronic renal denervation prevents glomerular hyperfiltration in diabetic rats," Nephrol Dial Transplant (2004) 19: 342-347.

Smithwick, R.H. et al., "Splanchnicectomy for essential hypertension," Journal Am Med Assn, 1953, 152 (16) 1501-1504.

Morrissey, D.M. et al, "Sympathectomy in the treatment of hypertension: Review of 122 cases," Lancet, 1953, 6757: 403-408.

Smithwick, R.H. et al., "Hypertension and associated cardiovascular disease: comparison of male and female mortality rates and their influence on selection of therapy," JAMA, 1956, 160: 1023-1033.

Evelyn KA, Singh MM, Chapman WP, Perera GA, Thaler H. Effect of thoracolumbar sympathectomy on the clinical course of primary (essential) hypertension. Am J Med. 1960. 188-221.

Onesti, G. et al., Blood pressure regulation in end-stage renal disease and anephric man, Circ Res Suppl., 1975, 36 & 37:145-152.

Hampers, C.L. et al, "A hemodynamic evaluation of bilateral nephrectomy and hemodialysis in hypertensive man," Circulation, 1967 (35); 272-288.

Curtis, J.J. et al., "Surgical therapy for persistent hypertension after renal transplantation," Transplantation, 1981, 31(2): 125-128.

Getts, R.T. et al., "Regression of left ventricular hypertrophy after bilateral nephrectomy," Nephrol Dial Transplant, 2006, vol. 21, pp. 1089-1091.

Devereaux R.B. et al., "Regression of Hypertensive Left Ventricular Hypertrophy by Losartan Compared With Atenolol: The Losartan Intervention for Endpoint Reduction in Hypertension (LIFE) Trial," Circulation, 2004, vol. 110, pp. 1456-1462.

Pitt B. et al., "Effects of Eplerenone, Enalpril, and Eplerenone/Enalapril in Patients With Essential Hypertension and Left Ventricular Hypertrophy: The 4E-Left Ventricular Hypertrophy Study," Circulation, 2003, vol. 108, pp. 1831-1838.

Chin J.L. et al., "Renal autotranplantation for the loin pain-hematuria syndrome: long term follow up of 26 cases," J Urol, 1998, vol. 160. pp. 1232-1236.

Gazdar A.F. and G.J. Dammin, "Neural degeneration and regeneration in human renal transplants," NEJM, Jul. 30, 1970, 283:222-224.

Shannon, J.L. et al. "Studies on the innervation of human renal allografts," J Pathol., 1998, vol. 186, pp. 109-115.

Hansen, J.M. et al, "The transplanted human kidney does not achieve functional reinnervation," Clin Science, 1994, vol. 87, pp. 13-20.

Kaye, D.M. et al., "Functional and neurochemical evidence for partial cardiac sympathetic reinnervation after cardiac transplantation in humans," Circulation, 1993, vol. 88, pp. 1101-1109.

Bhandari, A. and Ellias, M., "Loin pain hematuria syndrome: Pain control with RFA to the *Splanchanic plexus*," The Pain Clinic, 2000, vol. 12, No. 4, pp. 323-327.

Osborn, Jeffrey L. et al., "Effect of Renal Nerve Stimulation on Renal Blood Flow Autoregulation and Antinatriuresis During Reductions in Renal Perfusion Pressure", Proceedings of the Society for Experimental Biology and Medicine, vol. 168, pp. 77-81, 1981.

U.S. Appl. No. 60/236,420, Harrison et al.

"Atrial Fibrillation" Heart and Vascular Health on Yahoo! Health. 2 pages. <URL:http://health.yahoo.com/topic/heart/overview/article/healthwise/hw160872;_ylt=AiBT43Ey74HQ7ft3jAb4C.sPu7cF>.

"Heart Arrhythmia" Heart and Vascular Health on Yahoo! Health. 13 pages. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF>.

"Isovue: Data Sheet". Regional Health Limited. 8 pages. Mar. 11, 2003.

"Micro ETS Hyperhidrosis USA" Hyperhidrosis USA. 2 pages. <URL: http://www.hyperhidrosis-usa.com/Index.html>.

Amersham Health. "Hypaque-Cysto" 6 pages. 2003.

Arentz, Thomas et al. "Incidence of pulmonary vein stenosis 2 years after radiofrequency catheter ablation of refractory atrial fibrillation." European Heart Journal. 2003. 24; pp. 963-969.

Augustyniak, Robert A. et al., "Sympathetic Overactivity as a Cause of Hypertension in Chronic Renal Failure," Aug. 14, 2001, Journal of Hypertension, 2002, vol. 20, 2002 Lippincott Williams & Wilkins, pp. 3-9.

Boehmer, John P. "Resynchronization Therapy for Chronic CHF: Indications, Devices and Outcomes". Penn State College of Medicine: Penn State Heart and Vascular Institute. Transcatheter Cardiovascular Therapeutics 2005. 31 slides.

Bourge, Robert C. "Heart Failure Monitoring Devices: Rationale and Status" 28 pages.

Burkhoff, Daniel. "Interventional Device-Based Therapy For CHF Will Redefine Current Treatment Paradigms" Columbia University. 2004. 32 slides.

Canbaz, Suat et al. "Electrophysiological evaluation of phrenic nerve injury during cardiac surgery—a prospective, controlled clinical study." BioMed Central. 5 pages. 2004.

Carson, Peter. "Device-based Treatment For Chronic Heart Failure: Electrical Modulation of Myocardial Contractility". Transcatheter Cardiovascular Therapeutics 2005. 21 slides.

Chiou, CW et al. "Efferent Vagal Innervation of the Canine Atria and Sinus and Atrioventricular Nodes". Circulation. Jun. 1997. 95(11):2573-2584. Abstract only. 2 pages.

Cryovascular Systems, Inc. "Pre-Clinical Testing Establishing Parameters". PowerPoint Presentation. 18 slides.

Daniel, Alan and Honig, Carl R. "Does Histamine Influence Vasodilation Caused by Prolonged Arterial Occlusion or Heavy Exercise?" The Journal of Pharmacology and Experimental Therapeutics. vol. 215 No. 2. Aug. 21, 1980. pp. 533-538.

Dibona, Gerald F., "Sympathetic Nervous System and the Kidney in Hypertension," Current Opinion in Nephrology and Hypertension 2002, vol. 11, 2002 Lippincott Williams & Wilkins, pp. 197-200.

Dong, Jun et al. "Incidence and Predictors of Pulmonary Vein Stenosis Following Catheter Ablation of Atrial Fibrillation Using the Anatomic Pulmonary Vein Ablation Approach: Results from Paired Magnetic Resonance Imaging." Journal of Cardiovascular Electrophysiology. vol. 16, No. 8, Aug. 2005. pp. 845-852.

Fava, M. "Clinical Testing Establishing Safety & Efficacy", PowerPoint Presentation, Cryovascular Systems, Inc. 14 slides.

Fava, M. et al. "Initial Human Experience with CryoPlasty™ in the Treatment of Infrainguinal Arterial Disease." Abstract. 1 page.

Fischell, Tim A. et al. "Ultrasonic Energy: Effects on Vascular Function and Integrity." Circulation: Journal of the American Heart Association. 1991. 84:pp. 1783-1795.

Hodgkin, Douglas D. et al. "Electrophysiologic Characteristics of a Pulsed Iontophoretic Drug-Delivery System in Coronary Arteries." Journal of Cardiovascular Pharmacology. 29(1):pp. 39-44, Jan. 1997. Abstract. 2 pages.

Jia, Jianping and Pollock, Martin. "The pathogenesis of non-freezing cold nerve injury: Observations in the rat," Brain, 120; pp. 631-646, 1997.

Jia, Jianping et al. "Cold injury to nerves is not due to ischaemia alone." Brain. 121;pp. 989-1001. 1998.

Jin, Yuanzhe. Et al. "Pulmonary Vein Stenosis and Remodeling After Electrical Isolation for Treatment of Atrial Fibrillation: Short- and Medium-Term Follow-Up." PACE, vol. 27. pp. 1362-1370. Oct. 2004.

Joye, James D. and Tatsutani, Kristine. "In Vitro Studies of Arterial Freezing Injury". 4 pages.

Joye, James D. and Tatsutani, Kristine. "In Vivo Study of Endovascular Cryotherapy for the Prevention of Restenosis." 4 pages.

Knot, Harm J. and Nelson, Mark T. "Regulation of arterial diameter and wall [Ca2+] in cerebral arteries of rat by membrane potential and intravascular pressure." The Journal of Physiology. 1998. 508; pp. 199-209.

Kok, Lai Chow et al. "Effect of Heating on Pulmonary Veins: How to Avoid Pulmonary Vein Stenosis." Journal of Cardiovascular Electrophysiology. vol. 14, No. 3, Mar. 2003. pp. 250-254.

Mathur, Vandana S. "Intra-Renal Drug Delivery for Fluid Overload". FlowMedica. Transcatheter Cardiovascular Therapeutics 2005. 31 slides.

Mehran, Roxana. "Renal insufficiency and contrast nephropathy: The most common, least understood risk factor" Cardiovascular Research Foundation. Columbia University Medical Center. 2005. 86 slides.

Packer, Douglas L. et al. "Clinical Presentation, Investigation, and Management of Pulmonary Vein Stenosis Complicating Ablation for Atrial Fibrillation." Circulation: Journal of the American Heart Association. Feb. 8, 2005, pp. 546-554.

Pappone, Carlo and Santinelli, Vincerzo. "[2005][P2-70] Safety Report of Circumferential Pulmonary Vein Ablation. A 9-Year Single-Center Experience on 6,442 Patients with Atrial Fibrillation." Abstract only. 1 page.

Pappone, Carlo et al. "[2004][759] Pulmonary Vein Denervation Benefits Paroxysmal Atrial Fibrillation Patients after Circumferential Ablation." Abstract only. 1 page.

Purerfellner, Helmut and Martinek, Martin. "Pulmonary vein stenosis following catheter ablation of atrial fibrillation." Current Opinion in Cardiology. 20; pp. 484-490. 2005.

Purerfellner, Helmut et al. "Pulmonary Vein Stenosis by Ostial Irrigated-Tip Ablation: Incidence, Time Course, and Prediction." Journal of Cardiovascular Electrophysiology. vol. 14, No. 2. Feb. 2003. pp. 158-164.

Saad, Eduardo B. et al. "Pulmonary Vein Stenosis After Radiofrequency Ablation of Atrial Fibrillation: Functional Characterization, Evolution, and Influence of the Ablation Strategy." Circulation. 108; pp. 3102-3107. 2003.

Sabbah, Hani N. "Animal Models for Heart Failure and Device Development". Henry Ford Health System. 24 slides.

Schauerte, P et al. "Catheter ablation of cardiac autonomic nerves for prevention of vagal atrial fibrillation." Circulation. 102(22). Nov. 28, 2000. Abstract only. 2 pages.

Schauerte, P et al. "Focal atrial fibrillation: experimental evidence for a pathophysiologic role of the autonomic nervous system." Journal of Cardiovascular Electrophysiology. 12(5). May 2001. Abstract only. 2 pages.

Schauerte, P et al. "Transvenous parasympathetic nerve stimulation in the inferior vena cava and atrioventricular conduction." Journal of Cardiovascular Electrophysiology, 11(1). Jan. 2000. Abstract only. 2 pages.

Scherlag, BJ and Po, S. "The intrinsic cardiac nervous system and atrial fibrillation." Current Opinion in Cardiology. 21(1)151-54, Jan. 2006. Abstract only. 2 pages.

Schmitt, Joseph et al. "Intravascular Optical Coherence Tomography—Opening a Window into Coronary Artery Disease". LightLab Imaging, Inc. Business Briefing: European Cardiology 2005.

Serrador, Jorge M. "Autonomic Regulation of the Cardiovascular System" MIT Lecture. 8 pages, 48 slides.

Siegel, RJ et al. "Clinical demonstration that catheter-delivered ultrasound energy reverses arterial vasoconstriction." Journal of the American College of Cardiology. 1992. 20; 732-735. Summary only. 2 pages.

Sobotka, Paul A. "Treatment Strategies for Fluid Overload, CHF Patients". CHF Solutions. Transcatheter Cardiovascular Therapeutics 2005. 20 slides.

Steffen, W. et al. "Catheter-delivered high intensity, low frequency ultrasound induces vasodilation in vivo" European Heart Journal. 1994, 15;pp. 369-376.

Steg, PG et al. "Pulsed ultraviolet laser irradiation produces endothelium-independent relaxation of vascular smooth muscle". Circulation: Journal of the American Heart Association. 1989. pp. 189-197.

Taka, Tomomi et al. "Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats". Pathophysiology of Haemostasis and Thrombosis. Dec. 23, 2002, pp. 184-189.

Tamborero, David et al. "Incidence of Pulmonary Vein Stenosis in Patients Submitted to Atrial Fibrillation Ablation: A Comparison of the Selective Segmental Ostial Ablation vs. the Circumferential Pulmonary Veins Ablation." Journal of Intervocational Cardiac Electrophysiology. 14; pp. 41-25. 2005.

Terashima, Mitsuyasu et al. "Feasibility and Safety of a Novel CryoPlasty™ System". Poster. 1 page.

Thomas, John R. and Oakley, E. Howard N. "Chapter 15: Nonfreezing Cold Injury" *Medical Aspects of Harsh Environments*, vol. 1. pp. 467-490.

Vince, D. Geoffrey. "Virtual Histology: A new technique for the assessment of plaque composition". The Cleveland Clinic Foundation. 28 pages.

Yu, Wen-Chung et al. "Acquired Pulmonary Vein Stenosis after Radiofrequency Catheter Ablation of Paroxysmal Atrial Fibrillation." Journal of Cardiovascular Electrophysiology. vol. 12, No. 8. Aug. 2001. pp. 887-892.

RENAL NERVE STIMULATION METHOD AND APPARATUS FOR TREATMENT OF PATIENTS

RELATED APPLICATIONS

This application is a continuation of U.S. patent application Ser. No. 10/408,665, filed on Apr. 8, 2003, entitled "Renal Nerve Stimulation Method And Apparatus For Treatment of Patients," now U.S. Pat. No. 7,162,303, issued Jan. 9, 2007. This application is related to (a) U.S. patent application Ser. No. 11/145,122, filed on Jun. 3, 2005, entitled "Renal Nerve Stimulation Method And Apparatus For Treatment of Patients"; and (b) U.S. patent application Ser. No. 11/144,298, filed on Jun. 3, 2005, entitled "Renal Nerve Stimulation Method And Apparatus For Treatment of Patients", both of which are also continuation applications of U.S. patent application Ser. No. 10/408,665. U.S. patent application Ser. No. 10/408,665 is related and claims priority to the following commonly owned provisional applications: Ser. No. 60/370,190, entitled "Modulation Of Renal Nerve To Treat CHF," that was filed in the U.S. Patent and Trademark Office (USPTO) on Apr. 8, 2002; Ser. No. 60/415,575, entitled "Modulation Of Renal Nerve To Treat CHF," that was filed in the USPTO on Oct. 3, 2002, and Ser. No. 60/442,970, entitled "Treatment Of Renal Failure And Hypertension," that was filed in the USPTO on Jan. 29, 2003. The entirety of each of these applications is incorporated by reference herein.

FIELD OF THE INVENTION

This invention relates to methods and apparatus for treatment of congestive heart failure, chronic renal failure and hypertension by nerve stimulation. In particular, the invention relates to the improvement of these conditions of patients by blocking signals to the renal (kidney) nerve.

BACKGROUND OF THE INVENTION

The Heart Failure Problem

Congestive Heart Failure (CHF) is a form of heart disease still increasing in frequency. According to the American Heart Association, CHF is the "Disease of the Next Millennium". The number of patients with CHF is expected to grow even more significantly as an increasing number of the "Baby Boomers" reach 50 years of age. CHF is a condition that occurs when the heart becomes damaged and reduces blood flow to the organs of the body. If blood flow decreases sufficiently, kidney function becomes impaired and results in fluid retention, abnormal hormone secretions and increased constriction of blood vessels. These results increase the workload of the heart and further decrease the capacity of the heart to pump blood through the kidney and circulatory system. This reduced capacity further reduces blood flow to the kidney, which in turn further reduces the capacity of the blood. It is believed that the progressively-decreasing perfusion of the kidney is the principal non-cardiac cause perpetuating the downward spiral of the "Vicious Cycle of CHF". Moreover, the fluid overload and associated clinical symptoms resulting from these physiologic changes are predominant causes for excessive hospital admissions, terrible quality of life and overwhelming costs to the health care system due to CHF.

While many different diseases may initially damage the heart, once present, CHF is split into two types: Chronic CHF and Acute (or Decompensated-Chronic) CHF. Chronic Congestive Heart Failure is a longer term, slowly progressive, degenerative disease. Over years, chronic congestive heart failure leads to cardiac insufficiency. Chronic CHF is clinically categorized by the patient's ability to exercise or perform normal activities of daily living (such as defined by the New York Heart Association Functional Class). Chronic CHF patients are usually managed on an outpatient basis, typically with drugs.

Chronic CHF patients may experience an abrupt, severe deterioration in heart function, termed Acute Congestive Heart Failure, resulting in the inability of the heart to maintain sufficient blood flow and pressure to keep vital organs of the body alive. These acute CHF deteriorations can occur when extra stress (such as an infection or excessive fluid overload) significantly increases the workload on the heart in a stable chronic CHF patient. In contrast to the stepwise downward progression of chronic CHF, a patient suffering acute CHF may deteriorate from even the earliest stages of CHF to severe hemodynamic collapse. In addition, Acute CHF can occur within hours or days following an Acute Myocardial Infarction (AMI), which is a sudden, irreversible injury to the heart muscle, commonly referred to as a heart attack.

Normal Kidney Function:

The kidneys are a pair of organs that lie in the back of the abdomen on each side of the vertebral column. Kidneys play an important regulatory role in maintaining the homeostatic balance of the body. The kidneys function like a complex chemical plant. The kidneys eliminate foreign chemicals from the body, regulate inorganic substances and the extracellular fluid, and function as endocrine glands, secreting hormonal substances like renin and erythropoietin.

The main functions of the kidney are to maintain the water balance of the body and control metabolic homeostasis. Healthy kidneys regulate the amount of fluid in the body by making the urine more or less concentrated, thus either reabsorbing or excreting more fluid, respectively. In case of renal disease, some normal and important physiological functions become detrimental to the patient's health. This process is called overcompensation. In the case of Chronic Renal Failure (CRF) patients overcompensation often manifests in hypertension (pathologically high blood pressure) that is damaging to heart and blood vessels and can result in a stroke or death.

The functions of the kidney can be summarized under three broad categories: a) filtering blood and excreting waste products generated by the body's metabolism; b) regulating salt, water, electrolyte and acid-base balance; and c) secreting hormones to maintain vital organ blood flow. Without properly functioning kidneys, a patient will suffer water retention, reduced urine flow and an accumulation of wastes toxins in the blood and body.

The primary functional unit of the kidneys that is involved in urine formation is called the "nephron". Each kidney consists of about one million nephrons. The nephron is made up of a glomerulus and its tubules, which can be separated into a number of sections: the proximal tubule, the medullary loop (loop of Henle), and the distal tubule. Each nephron is surrounded by different types of cells that have the ability to secrete several substances and hormones (such as renin and erythropoietin). Urine is formed as a result of a complex process starting with the filtration of plasma water from blood into the glomerulus. The walls of the glomerulus are freely permeable to water and small molecules but almost impermeable to proteins and large molecules. Thus, in a healthy kidney, the filtrate is virtually free of protein and has no cellular elements. The filtered fluid that eventually becomes urine flows through the tubules. The final chemical composition of the urine is determined by the secretion into and reabsorbtion of substances from the urine required to maintain homeostasis.

Receiving about 20% of cardiac output, the two kidneys filter about 125 ml of plasma water per minute. This is called the Glomerular Filtration Rate (GFR) and is the gold standard measurement of the kidney function. Since measurement of GFR is very cumbersome and expensive, clinically, the serum creatinine level or creatinine clearance are used as surrogates to measure kidney function. Filtration occurs because of a pressure gradient across the glomerular membrane. The pressure in the arteries of the kidney pushes plasma water into the glomerulus causing filtration. To keep the GFR relatively constant, pressure in the glomerulus is held constant by the constriction or dilatation of the afferent and efferent arterioles, the muscular walled vessels leading to and from each glomerulus.

Abnormal Kidney Function in CHF:

The kidneys maintain the water balance of the body and control metabolic homeostasis. The kidneys regulate the amount of fluid in the body by making the urine more or less concentrated, thus either reabsorbing or excreting more fluid, respectively. Without properly functioning kidneys, a patient will suffer water retention, reduced urine flow and an accumulation of wastes toxins in the blood and body. These conditions resulting from reduced renal function or renal failure (kidney failure) are believed to increase the workload of the heart. In a CHF patient, renal failure will cause the heart to further deteriorate as the water build-up and blood toxins accumulate due to the poorly functioning kidneys and in turn, cause the heart further harm.

In a CHF patient, for any of the known cause of heart dysfunction, the heart will progressively fail and blood flow and pressure will drop in the patient's circulatory system. In the acute heart failure, the short-term compensations serve to maintain perfusion to critical organs, notably the brain and the heart that cannot survive prolonged reduction in blood flow. In chronic heart failure, these same responses that initially aided survival in acute heart failure can become deleterious.

A combination of complex mechanisms contribute to the deleterious fluid overload in CHF. As the heart fails and blood pressure drops, the kidneys cannot function owing to insufficient blood pressure for perfusion and become impaired. This impairment in renal function ultimately leads to a decrease in urine output. Without sufficient urine output, the body retains fluids and the resulting fluid overload causes peripheral edema (swelling of the legs), shortness of breath (from fluid in the lungs), and fluid in the abdomen, among other undesirable conditions in the patient.

In addition, the decrease in cardiac output leads to reduced renal blood flow, increased neurohormonal stimulus, and release of the hormone renin from the juxtaglomerular apparatus of the kidney. This results in avid retention of sodium and thus volume expansion. Increased rennin results in the formation of angiotensin, a potent vasoconstrictor.

Heart failure and the resulting reduction in blood pressure reduces the blood flow and perfusion pressure through organs in the body, other than the kidneys. As they suffer reduced blood pressure, these organs may become hypoxic causing the development of a metabolic acidosis which reduces the effectiveness of pharmacological therapy as well as increases the risk of sudden death.

This spiral of deterioration that physicians observe in heart failure patients is believed to be mediated, in large part, by activation of a subtle interaction between heart function and kidney function, known as the renin-angiotensin system. Disturbances in the heart's pumping function results in decreased cardiac output and diminished blood flow. The kidneys respond to the diminished blood flow as though the total blood volume was decreased, when in fact the measured volume is normal or even increased. This leads to fluid retention by the kidneys and formation of edema causing fluid overload and increased stress on the heart.

Systemically, CHF is associated with an abnormally elevated peripheral vascular resistance and is dominated by alterations of the circulation resulting from an intense disturbance of sympathetic nervous system function. Increased activity of the sympathetic nervous system promotes a downward vicious cycle of increased arterial vasoconstriction (increased resistance of vessels to blood flow) followed by a further reduction of cardiac output, causing even more diminished blood flow to the vital organs.

In CHF via the previously explained mechanism of vasoconstriction, the heart and circulatory system dramatically reduces blood flow to kidneys. During CHF, the kidneys receive a command from higher neural centers via neural pathways and hormonal messengers to retain fluid and sodium in the body. In response to stress on the heart, the neural centers command the kidneys to reduce their filtering functions. While in the short term, these commands can be beneficial, if these commands continue over hours and days they can jeopardize the persons life or make the person dependent on artificial kidney for life by causing the kidneys to cease functioning.

When the kidneys do not fully filter the blood, a huge amount of fluid is retained in the body resulting in bloating (fluid in tissues), and increases the workload of the heart. Fluid can penetrate into the lungs and the patient becomes short of breath. This odd and self-destructive phenomenon is most likely explained by the effects of normal compensatory mechanisms of the body that improperly perceive the chronically low blood pressure of CHF as a sign of temporary disturbance such as bleeding.

In an acute situation, the organism tries to protect its most vital organs, the brain and the heart, from the hazards of oxygen deprivation. Commands are issued via neural and hormonal pathways and messengers. These commands are directed toward the goal of maintaining blood pressure to the brain and heart, which are treated by the body as the most vital organs. The brain and heart cannot sustain low perfusion for any substantial period of time. A stroke or a cardiac arrest will result if the blood pressure to these organs is reduced to unacceptable levels. Other organs, such as kidneys, can withstand somewhat longer periods of ischemia without suffering long-term damage. Accordingly, the body sacrifices blood supply to these other organs in favor of the brain and the heart.

The hemodynamic impairment resulting from CHF activates several neurohomonal systems, such as the renin-angiotensin and aldosterone system, sympatho-adrenal system and vasopressin release. As the kidneys suffer from increased renal vasoconstriction, the filtering rate (GFR) of the blood drops and the sodium load in the circulatory system increases. Simultaneously, more renin is liberated from the juxtaglomerular of the kidney. The combined effects of reduced kidney functioning include reduced glomerular sodium load, an aldosterone-mediated increase in tubular reabsorption of sodium, and retention in the body of sodium and water. These effects lead to several signs and symptoms of the CHF condition, including an enlarged heart, increased systolic wall stress, an increased myocardial oxygen demand, and the formation of edema on the basis of fluid and sodium retention in the kidney. Accordingly, sustained reduction in renal blood flow and vasoconstriction is directly responsible for causing the fluid retention associated with CHF.

In view of the physiologic mechanisms described above it is positively established that the abnormal activity of the kidney is a principal non-cardiac cause of a progressive condition in a patient suffering from CHF.

Growing population of late stage CHF patients is an increasing concern for the society. The disease is progressive, and as of now, not curable. The limitations of drug therapy and its inability to reverse or even arrest the deterioration of CHF patients are clear. Surgical therapies are effective in some cases, but limited to the end-stage patient population because of the associated risk and cost. There is clearly a need for a new treatment that will overcome limitations of drug therapy but will be less invasive and costly than heart transplantation.

Similar condition existed several decades ago in the area of cardiac arrhythmias. Limitations of anti-arrhythmic drugs were overcome by the invention of heart pacemakers. Widespread use of implantable electric pacemakers resulted in prolonged productive life for millions of cardiac patients. So far, all medical devices proposed for the treatment of CHF are cardio-centric i.e., focus on the improvement of the heart function. The dramatic role played by kidneys in the deterioration of CHF patients has been overlooked by the medical device industry.

Neural Control of Kidneys:

The autonomic nervous system is recognized as an important pathway for control signals that are responsible for the regulation of body functions critical for maintaining vascular fluid balance and blood pressure. The autonomic nervous system conducts information in the form of signals from the body's biologic sensors such as baroreceptors (responding to pressure and volume of blood) and chemoreceptors (responding to chemical composition of blood) to the central nervous system via its sensory fibers. It also conducts command signals from the central nervous system that control the various innervated components of the vascular system via its motor fibers.

Experience with human kidney transplantation provided early evidence of the role of the nervous system in the kidney function. It was noted that after the transplant, when all the kidney nerves are totally severed, the kidney increased the excretion of water and sodium. This phenomenon was also observed in animals when the renal nerves were cut or chemically destroyed. The phenomenon was called "denervation diuresis" since the denervation acted on a kidney similar to a diuretic medication. Later the "denervation diuresis" was found to be associated with the vasodilatation the renal arterial system that led to the increase of the blood flow through the kidney. This observation was confirmed by the observation in animals that reducing blood pressure supplying the kidney could reverse the "denervation diuresis".

It was also observed that after several months passed after the transplant surgery in successful cases, the "denervation diuresis" in transplant recipients stopped and the kidney function returned to normal. Originally it was believed that the "renal diuresis" is a transient phenomenon and that the nerves conducting signals from the central nervous system to the kidney are not essential for the kidney function. Later, new discoveries led to the different explanation. It is believed now that the renal nerves have a profound ability to regenerate and the reversal of the "denervation diuresis" shall be attributed to the growth of the new nerve fibers supplying kidneys with the necessary stimuli.

Another body of research that is of particular importance for this application was conducted in the period of 1964-1969 and focused on the role of the neural control of secretion of the hormone renin by the kidney. As was discussed previously, renin is a hormone responsible for the "vicious cycle" of vasoconstriction and water and sodium retention in heart failure patients. It was demonstrated that increase (renal nerve stimulation) or decrease (renal nerve denervation) in renal sympathetic nerve activity produced parallel increases and decreases in the renin secretion rate by the kidney, respectively.

In summary, it is known from clinical experience and the large body of animal research that the stimulation of the renal nerve leads to the vasoconstriction of blood vessels supplying the kidney, decreased renal blood flow, decreased removal of water and sodium from the body and increased renin secretion. These observations closely resemble the physiologic landscape of the deleterious effects of the chronic congestive heart failure. It is also known that the reduction of the sympathetic renal nerve activity, achieved by denervation, can reverse these processes.

It was established in animal models that the heart failure condition results in the abnormally high sympathetic stimulation of the kidney. This phenomenon was traced back to the sensory nerves conducting signals from baroreceptors to the central nervous system. Baroreceptors are the biologic sensors sensitive to blood pressure. They are present in the different locations of the vascular system. Powerful relationship exists between the baroreceptors in the carotid arteries (supplying brain with arterial blood) and the sympathetic nervous stimulus to the kidneys. When the arterial blood pressure was suddenly reduced in experimental animals with heart failure, the sympathetic tone increased. Nevertheless the normal baroreflex alone, cannot be responsible for the elevated renal nerve activity in chronic CHF patients. If exposed to the reduced level of arterial pressure for a prolonged time baroreceptors normally "reset" i.e. return to the baseline level of activity until a new disturbance is introduced. Therefore, in chronic CHF patients the components of the autonomic nervous system responsible for the control of blood pressure and the neural control of the kidney function become abnormal. The exact mechanisms that cause this abnormality are not fully understood but, its effects on the overall condition of the CHF patients are profoundly negative.

End Stage Renal Disease Problem:

There is a dramatic increase in patients with end-stage renal disease (ESRD) due to diabetic nephropathy, chronic glomerulonephritis and uncontrolled hypertension. In the US alone, 372,000 patients required dialysis in the year 2000. There were 90,000 new cases of ESRD in 1999 with the number of patients on dialysis is expected to rise to 650,000 by the year 2010. The trends in Europe and Japan are forecasted to follow a similar path. Mortality in patients with ESRD remains 10-20 times higher than that in the general population. Annual Medicare patient costs $52,868 for dialysis and $18,496 for transplantation. The total cost for Medicare patients with ESRD in 1998 was $12.04 billion.

The primary cause of these problems is the slow relentless progression of Chronic Renal Failure (CRF) to ESRD. CRF represents a critical period in the evolution of ESRD. The signs and symptoms of CRF are initially minor, but over the course of 2-5 years, become progressive and irreversible. Until the 1980's, there were no therapies that could significantly slow the progression of CRF to ESRD. While some progress has been made in combating the progression to and complications of ESRD in last two decades, the clinical benefits of existing interventions remain limited with no new drug or device therapies on the horizon.

Progression of Chronic Renal Failure:

It has been known for several decades that renal diseases of diverse etiology (hypotension, infection, trauma, autoimmune disease, etc.) can lead to the syndrome of CRF characterized by systemic hypertension, proteinuria (excess protein filtered from the blood into the urine) and a progressive decline in GFR ultimately resulting in ESRD. These observations suggested that CRF progresses via a common pathway of mechanisms, and that therapeutic interventions inhibiting this common pathway may be successful in slowing the rate of progression of CRF irrespective of the initiating cause.

To start the vicious cycle of CRF, an initial insult to the kidney causes loss of some nephrons. To maintain normal GFR, there is an activation of compensatory renal and systemic mechanisms resulting in a state of hyperfiltration in the remaining nephrons. Eventually, however, the increasing numbers of nephrons "overworked" and damaged by hyperfiltration are lost. At some point, a sufficient number of nephrons are lost so that normal GFR can no longer be maintained. These pathologic changes of CRF produce worsening systemic hypertension, thus high glomerular pressure and increased hyperfiltration. Increased glomerular hyperfiltration and permeability in CRF pushes an increased amount of protein from the blood, across the glomerulus and into the renal tubules. This protein is directly toxic to the tubules and leads to further loss of nephrons, increasing the rate of progression of CRF. This vicious cycle of CRF continues as the GFR drops, with loss of additional nephrons leading to further hyperfiltration and eventually to ESRD requiring dialysis. Clinically, hypertension and excess protein filtration have been shown to be two major determining factors in the rate of progression of CRF to ESRD.

Though previously clinically known, it was not until the 1980s that the physiologic link between hypertension, proteinuria, nephron loss and CRF was identified. In 1990s the role of sympathetic nervous system activity was elucidated. Afferent signals arising from the damaged kidneys due to the activation of mechanoreceptors and chemoreceptors stimulate areas of the brain responsible for blood pressure control. In response brain increases sympathetic stimulation on the systemic level resulting in the increased blood pressure primarily through vasoconstriction of blood vessels.

When elevated sympathetic stimulation reaches the kidney via the efferent sympathetic nerve fibers, it produces major deleterious effects in two forms:

A. Kidney is damaged by direct renal toxicity from the release of sympathetic neurotransmitters (such as norepinephrine) in the kidney independent of the hypertension.

B. Secretion of renin that activates Angiotensin II is increased leading to the increased systemic vasoconstriction and exacerbated hypertension.

Over time damage to the kidney leads to further increase of afferent sympathetic signals from the kidney to the brain. Elevated Angiotensin II further facilitates internal renal release of neurotransmitters. The feedback loop is therefore closed accelerating the deterioration of the kidney.

BRIEF DESCRIPTION OF THE INVENTION

A treatment of heart failure, renal failure and hypertension has been developed to arrest or slow down the progression of the disease. This treatment is expected to delay the morbid conditions and death often suffered by CHF patients and to delay the need for dialysis in renal failure. This treatment is expected to control hypertension in patients that do not respond to drugs or require multiple drugs.

The treatment includes a device and method that reduces the abnormally elevated sympathetic nerve signals that contribute to the progression of heart and renal disease. The desired treatment should be implemented while preserving a patient's mobility and quality of life without the risk of major surgery.

The treatment breaks with tradition and proposes a counterintuitive novel method and apparatus of treating heart failure, renal failure and hypertension by electrically or chemically modulating the nerves of the kidney. Elevated nerve signals to and from the kidney are a common pathway of the progression of these chronic conditions.

Chronic heart and renal failure is treated by reducing the sympathetic efferent or afferent nerve activity of the kidney. Efferent nerves (as opposed to afferent) are the nerves leading from the central nervous system to the organ, in this case to the kidney. Sympathetic nervous system (as opposed to parasympathetic) is the part of the autonomic nervous system that is concerned especially with preparing the body to react to situations of stress or emergency that tends to depress secretion, decrease the tone and contractility of smooth muscle, and increase heart rate. In the case of renal sympathetic activity, it is manifested in the inhibition of the production of urine and excretion of sodium. It also elevates the secretion of renin that triggers vasoconstriction. This mechanism is best illustrated by the response of the body to severe bleeding. When in experimental animals, the blood pressure is artificially reduced by bleeding, and the sympathetic inhibition of the kidney is increased to maintain blood pressure with an ultimate goal of preserving the brain from hypotension. The resulting vasoconstriction and fluid retention work in synchrony to help the body to maintain homeostasis.

Efferent renal nerve activity is considered postganglionic, autonomic and exclusively sympathetic. In general, efferent sympathetic nerves can cause a variety of responses in the innervated organs. Studies of sympathetic renal nerves show that they have a strong tendency to behave as a uniform population that acts as vasoconstrictors. The renal postganglionic neurons are modulated by pregangleonic (ganglion is a "knot" or agglomeration of nerve sells) nerves that originate from the brain and thoracic and upper lumbar regions of the spinal cord.

The pregangleonic nerves have diverse function and are likely to have high degree of redundancy. Although different pathways exist to achieve reduced efferent renal nerve activity, the simplest way is to denervate the postganglionic nerves with an electric stimulus or a chemical agent. The same desired affect could be achieved by total surgical, electric or chemical destruction (ablation) of the nerve. For two reasons this is not a preferred pathway. As was described before, renal nerves regenerate and can grow back as soon as several months after surgery. Secondarily, total irreversible denervation of the kidney can result in danger to the patient. Overdiuresis or removal of excess water from blood can result in the reduction of blood volume beyond the amount that can be rapidly replaced by fluid intake. This can result in hypovolemia and hypotension. Hypotension is especially dangerous in heart failure patients with the reduced capacity of the heart to pump blood and maintain blood pressure. In addition, the vasodilation of the renal artery resulting from the renal denervation will cause a significant increase in renal blood flow. In a healthy person, renal blood flow can amount to as much as 20% of the total cardiac output. In heart failure patients cardiac output is reduced and the renal denervation can "steal" even larger fraction of it from circulation. This, in turn, can lead to hypotension. Also, in a heart failure patient the heart has limited ability to keep up with the demand for oxygenated blood that can be caused by even modest physical effort. Therefore a heart failure patient that can sustain the increased blood flow to the kidneys while at rest can face serious complications resulting from acute hypotension, if the demand for blood flow is increased by temperature change or exercise.

In view of the factors described above it is desired to have means to reduce the efferent sympathetic stimulation of the kidney in CHF patients in a reversible, controlled fashion preferably based on a physiologic feedback signal that is indicative of the oxygen demand by the body, blood pressure, cardiac output of the patient or a combination of these and other physiologic parameters.

The treatment also breaks with tradition and proposes a counterintuitive novel method and apparatus of treating chronic renal failure (CRF) with the goal of slowing down the progression of CRF to the ESRD by electrically or chemically altering the sympathetic neural stimulation entering and exiting the kidney. The described method and apparatus can be also used to treat hypertension in patients with renal disease or abnormal renal function.

To control the afferent nerve signals from the kidney to the brain and block efferent nerve stimuli from entering the kidney (without systemic side effects of drug therapy), a renal nerve stimulator is implanted and attached to an electrode lead placed around or close to the renal artery. Stimulation effectively blocks or significantly reduces both efferent and afferent signals traveling between the kidney, the autonomic nervous system and the central nervous system.

The benefits that may be possible by controlling renal nerve signals to reduce efferent overstimulation are:

a. The secretion of renin by kidney should be reduced by 40-50% translating into the proportionate reduction of systemic angiotensin II, resulting in the reduction of blood pressure in all hypertensive patients including patients refractory to drugs.

b. Similar to renoprotective mechanisms of ACE-I, the reduction of angiotensin II should result in slowed progression of intrarenal changes in glomerular structure and function independent of blood pressure control.

c. Similar to the effects of moxonidine, reduced efferent overstimulation should reduce damage by direct renal toxicity from the release of sympathetic neurotransmitters.

Following the reduction of the afferent sympathetic renal feedback to the brain, there is expected to be a marked reduction in the systemic efferent overstimulation. This will translate into the systemic vasodilation and reduction of hypertension independent of the renin-angiotensin II mechanism.

Renal nerve stimulation in hypertensive CRF patients is unlikely to cause clinically relevant episodes of hypotension. Systemic blood pressure is tightly controlled by feedbacks from baroreceptors in aorta and carotid sinuses. These mechanisms are likely to take over if the blood pressure becomes too low. In polycystic kidney disease (PKD) patients who underwent surgery for total denervation of kidneys, denervation resolved hypertension without postoperative episodes of hypotension.

Technique for Nerve Modulation

Nerve activity can be reversibly modulated in several different ways. Nerves can be stimulated with electric current or chemicals that enhance or inhibit neurotransmission. In the case of electrical stimulation, a stimulator containing a power source is typically connected to the nerve by wires or leads. Leads can terminate in electrodes, cuffs that enclose the nerve or in conductive anchors (screws or hooks) that are embedded in tissue. In the later case, the lead is designed to generate sufficient electric field to alter or induce current in the nerve without physically contacting it. The electrodes or leads can by bipolar or unipolar. There are permanent leads that are implanted for months and years to treat a chronic condition and temporary leads used to support the patient during an acute stage of the disease. The engineering aspects of design and manufacturing of nerve stimulators, pacemakers, leads, anchors and nerve cuffs are well known.

Proposed clinical applications of nerve stimulation include: Depression, Anxiety, Alzheimer's Disease, Obesity, and others. In all existing clinical applications except pain control, the targeted nerves are stimulated to increase the intensity of the transmitted signal. To achieve relief of hypertension and CRF signal traffic traveling to and from the kidney via renal nerves needs to be reduced. This can be achieved by known methods previously used in physiologic studies on animals. A nerve can be paced with electric pulses at high rate or at voltage that substantially exceed normal traffic. As a result, a nerve will be "overpaced", run out of neurotransmitter substance and transmit less stimulus to the kidney. Alternatively relatively high voltage potential can be applied to the nerve to create a blockade. This method is known as "voltage clamping" of a nerve. Infusion of a small dose of a local anesthetic in the vicinity of the nerve will produce the same effect.

Ablation of conductive tissue pathways is another commonly used technique to control aterial or ventricular tachycardia of the heart. Ablation can be performed by introduction of a catheter into the venous system in close proximity of the sympathetic renal nerve subsequent ablation of the tissue. Catheter based ablation devices were previously used to stop electric stimulation of nerves by heating nerve tissue with RF energy that can be delivered by a system of electrodes. RF energy thus delivered stops the nerve conduction. U.S. Pat. No. 6,292,695 describes in detail a method and apparatus for transvascular treatment of tachycardia and fibrillation with nerve stimulation and ablation. Similar catheter based apparatus can be used to ablate the renal nerve with an intent to treat CRF. The method described in this invention is applicable to irreversible ablation of the renal nerve by electric energy, cold, or chemical agents such as phenol or alcohol.

Thermal means may be used to cool the renal nerve and adjacent tissue to reduce the sympathetic nerve stimulation of the kidney. Specifically, the renal nerve signals may be dampened by either directly cooling the renal nerve or the kidney, to reduce their sensitivity, metabolic activity and function, or by cooling the surrounding tissue. An example of this approach is to use the cooling effect of the Peltier device. Specifically, the thermal transfer junction may be positioned adjacent the vascular wall or a renal artery to provide a cooling effect. The cooling effect may be used to dampen signals generated by the kidney. Another example of this approach is to use the fluid delivery device to deliver a cool or cold fluid (e.g. saline).

BRIEF DESCRIPTION OF THE DRAWINGS

A preferred embodiment and best mode of the invention is illustrated in the attached drawings that are described as follows.

DETAILED DESCRIPTION OF THE INVENTION

A method and apparatus has been developed to regulate sympathetic nerve activity to the kidney to improve a patient's renal function and overall condition, and ultimately to arrest or reverse the vicious cycle of CHF disease.

Figure 1:
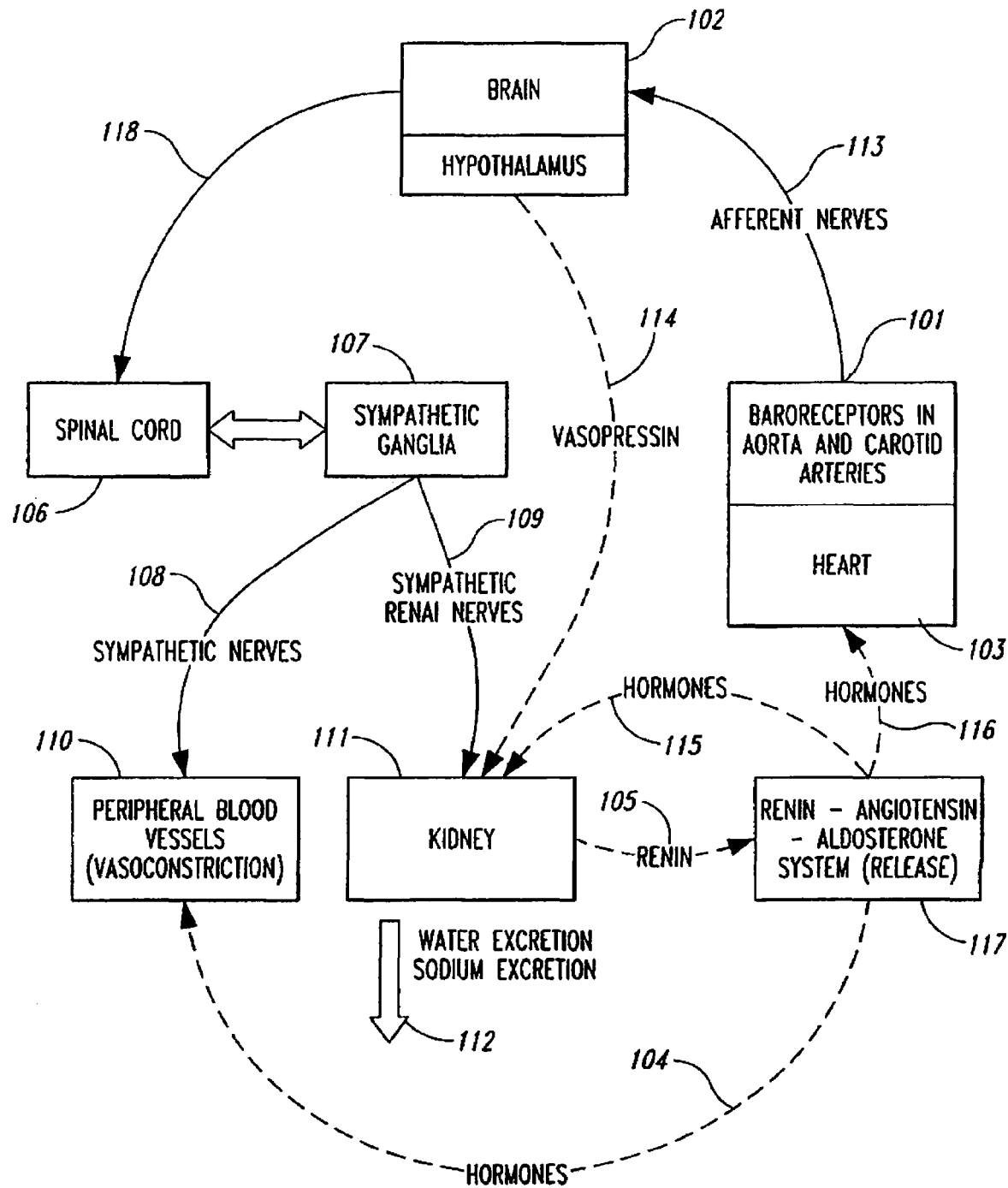
FIG. 1 illustrates the role of sympathetic renal nerve stimulation in congestive heart failure (CHF).

FIG. 1 illustrates the role of sympathetic renal nerves in heart failure. Neural pathways are indicated by solid lines, hormones by interrupted lines. Baroreceptors 101 respond to low blood pressure resulting from the reduced ability of the failing heart 103 to pump blood. Unloading of baroreceptors 101 in the left ventricle of the heart 103, carotid sinus, and aortic arch (not shown) generates afferent neural signals 113 that stimulate cardio-regulatory centers in the brain 102. This stimulation results in activation of efferent pathways in the sympathetic nervous system 118. Sympathetic signals are transmitted to the spinal cord 106, sympathetic ganglia 107 and via the sympathetic efferent renal nerve 109 to the kidney 111. The increased activity of sympathetic nerves 108 also causes vasoconstriction 110 (increased resistance) of peripheral blood vessels.

In the kidney 111 efferent sympathetic nerve stimulation 109 causes retention of water (reduction of the amount of urine) and retention of sodium 112 an osmotic agent that is responsible for the expansion of blood volume. The sympathetic stimulation of the kidney stimulates the release of hormones renin 105 and angiotensin 11. These hormones activate the complex renin-angiotensin-aldosterone system 117 leading to more deleterious hormones causing vasoconstriction 104 and heart damage 116. The sympathetic stimulation of the hypothalamus of the brain 102 results in the release of the powerful hormone vasopressin 114 that causes further vasoconstriction of blood vessels. Angiotensin II constricts blood vessels and stimulates the release of aldosterone from adrenal gland (not shown). It also increases tubular sodium reabsorption (sodium retention) in the kidney 111 and causes remodeling of cardiac myocytes therefore contributing to the further deterioration of the heart 103 and the kidney 111.

It can be inferred from the FIG. 1 that the renal efferent sympathetic stimulation in heart failure is caused by low blood pressure and is a primary factor responsible for the most debilitating symptom of heart failure i.e. fluid overload. It also contributes to the progression of the disease. Acting through the volume overload and peripheral vasoconstriction (together increasing load on the heart) it accelerates the enlargement of the left ventricle that in turn results in the deteriorating ability of the heart to pump blood. Drugs used to treat heat failure address these issues separately. Diuretics are used to reduce fluid overload by reducing the reabsorption of sodium and increasing the excretion of water 112. Vasodilators are used to reduce peripheral vasoconstriction 110 by reducing levels of angiotensin 117. Inotropic agents are used to increase blood pressure and de-activate the signals from baroreceptors 101. These drugs have limited affect and ultimately fail to control the progression and debilitating symptoms heart failure. The proposed invention corrects the neurohormonal misbalance in heart failure by directly controlling the sympathetic neural stimulation 109 of the kidney 111.

Figure 2:
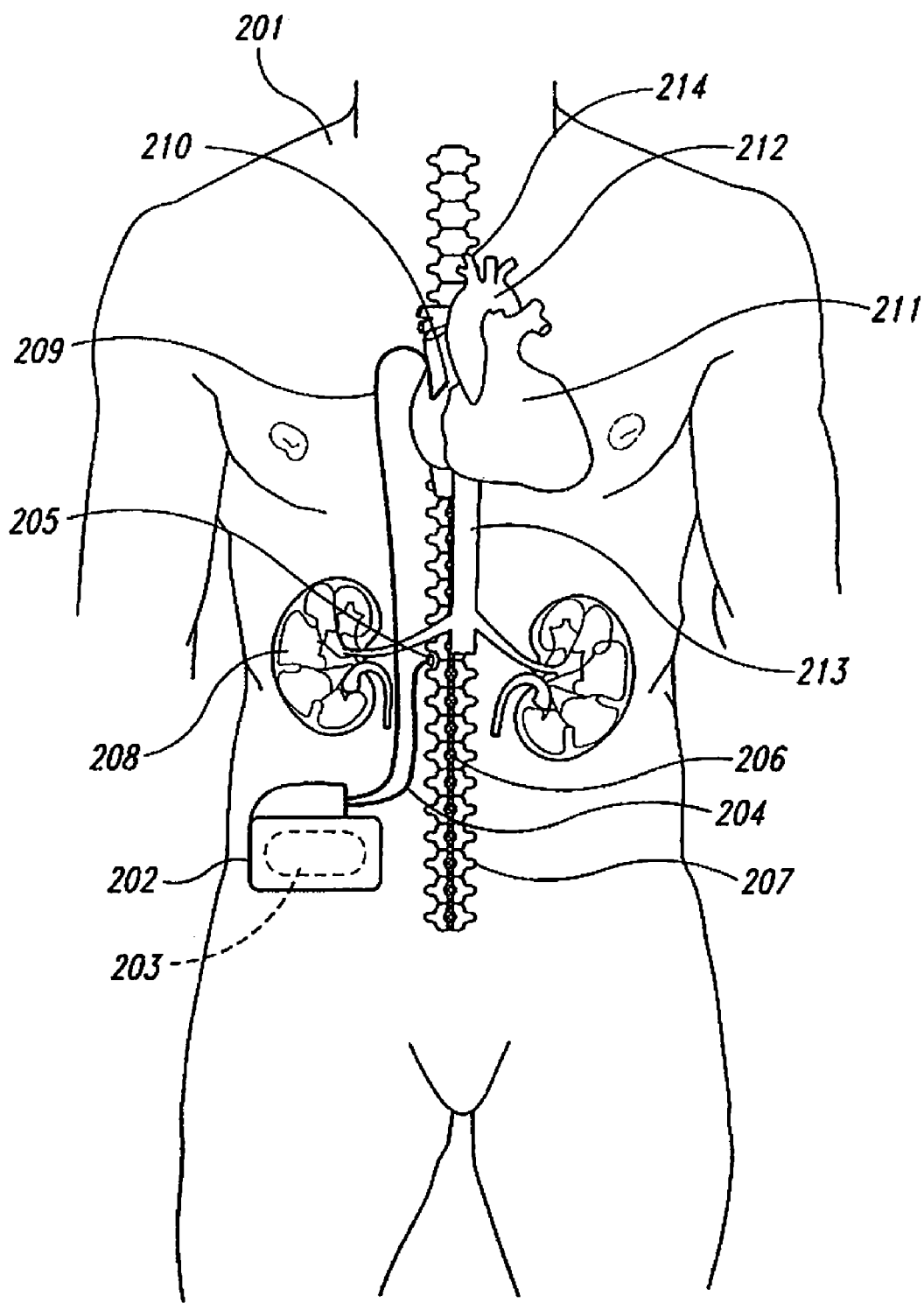
FIG. 2 illustrates the preferred implanted electrostimulation embodiment of the present invention.

FIG. 2 shows a patient 201 suffering from chronic congestive heart failure treated in accordance with the invention. An implantable device 202 is implanted in the patients body. An implantable device can be an electric device similar to a pacemaker or nerve stimulator or a chemical substance infusion device. Such devices are well known in the field of medicine. Internal mechanism of the implantable device typically includes a battery 203, an electronic circuit and (in the case of a drug delivery device) a reservoir with medication.

An example of an implantable drug infusion device is the MiniMed 2007™ implantable insulin pump system for treatment of diabetes or the SynchroMed Infusion System used to control chronic pain, both manufactured by Medtronic Inc. The drug used in this embodiment can be a common local anesthetic such as Novocain or Lidocaine or a more long lasting equivalent anesthetic. Alternatively, a nerve toxin such as the botox can be used to block the nerve. An example of an implantable nerve stimulator is the Vagus Nerve Stimulation (VNS™) with the Cyberonics NeuroCybernetic Prosthesis (NCP®) System used for treatment of epilepsy. It is manufactured by Cyberonics Inc. The internal mechanism of the implantable device typically includes a battery, an electronic circuit and (in the case of a drug delivery device), a reservoir with medication. Neurostimulation systems from different manufacturers are virtually identical across application areas, usually varying only in the patterns of stimulating voltage pulses, style or number of electrodes used, and the programmed parameters. The basic implantable system consists of a pacemaker-like titanium case enclosing the power source and microcircuitry that are used to create and regulate the electrical impulses. An extension lead attached to this generator carries the electrical pulses to the electrode lead that is implanted or attached to the nerves or tissues to be stimulated.

The implantable device 202 is equipped with the lead 204 connecting it to the renal nerve 205. The lead can contain an electric wire system or a catheter for delivery of medication or both. Renal nerve conducts efferent sympathetic stimulation from the sympathetic trunk 206 to the kidney 208. Sympathetic trunk is connected to the patient's spinal cord inside the spine 207. The connection can be located between the kidney 208 and the posterior renal or other renal ganglia (not shown) in the region of the $10^{th}$, $11^{th}$ and $12^{th}$ thoracic and $1^{st}$ lumbar segments of the spine 207.

The implantable device 202 is also equipped with the sensor lead 209 terminated with the sensor 210. The sensor can be a pressure sensor or an oxygen saturation sensor. The sensor 210 can be located in the left ventricle of the heart 211, right atrium of the heart or other cavity of the heart. It can also be located outside of the heart in the aorta 213, the aortic arch 212 or a carotid artery 214. If the sensor is a pressure sensor, it is used to supply the device 202 with the information necessary to safely regulate the sympathetic nerve signals to the kidney 208. A venous blood oxygen saturation signal can be used in a similar way to control the sympathetic nerve traffic based on oxygen demand. The sensor will be placed in the right atrium of the heart or in the vena cava. More than one sensor can be used in combination to supply information to the device. Sensors can be inside the vascular system (blood vessels) or outside of it. For example, a motion sensor can be used to detect activity of the person. Such sensor does not require placement outside the implanted device case and can be integrated inside the sealed case of the device 202 as a part of the internal mechanism.

Figure 3:
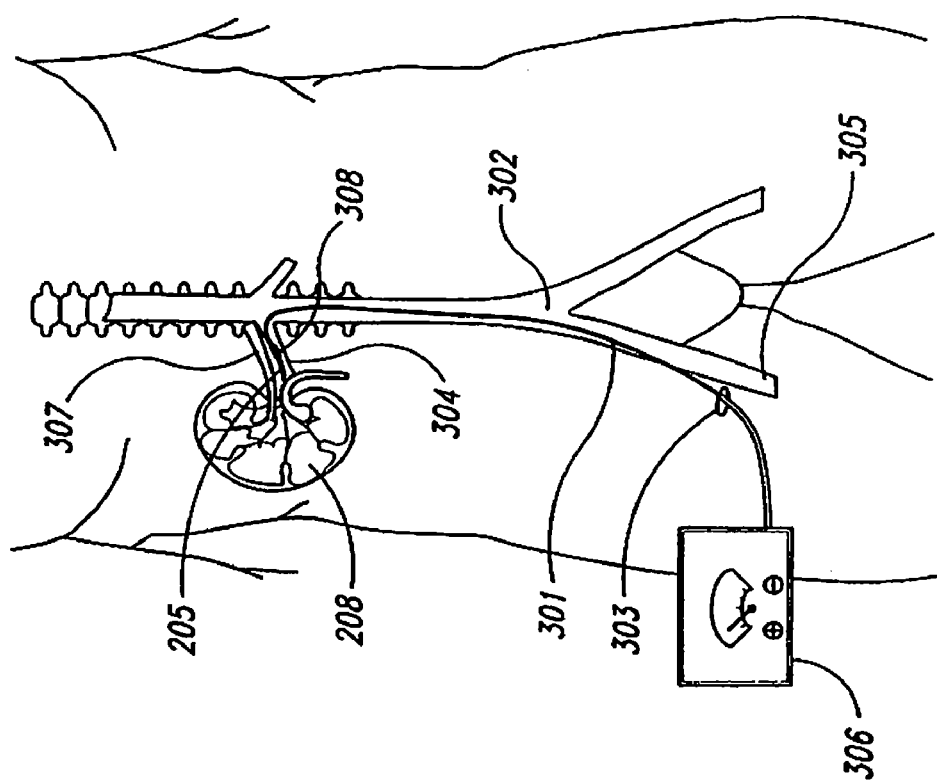
FIG. 3 illustrates stimulation of renal nerves across the wall of the renal vein.

FIG. 3 shows external renal nerve stimulator apparatus 306 connected to the electrode tip 308 by the catheter 301. A catheter is inserted via an insertion site 303 into the femoral vein 305 into the vena cava 302 and further into the renal vein 304. The tip 308 is then brought into the electric contact with the wall of the vein 304. Hooks or screws, similar to ones used to secure pacemaker leads, can be used to anchor the tip and improve the electric contact. The tip 308 can have one, two or more electrodes integrated in its design. The purpose of the electrodes is to generate the electric field sufficiently strong to influence traffic along the renal nerve 205 stimulating the kidney 208.

Two potential uses for the embodiment shown on FIG. 3 are the acute short-term stimulation of the renal nerve and the implanted embodiment. For short term treatment, a catheter equipped with electrodes on the tip is positioned in the renal vein. The proximal end of the catheter is left outside of the body and connected to the electro stimulation apparatus. For the implanted application, the catheter is used to position a stimulation lead, which is anchored in the vessel and left in place after the catheter is withdrawn. The lead is then connected to the implantable stimulator that is left in the body and the surgical site is closed. Patients have the benefit of mobility and lower risk of infection with the implanted stimulator—lead system.

Similar to the venous embodiment, an arterial system can be used. Catheter will be introduced via the femoral artery and aorta (not shown) into the renal artery 307. Arterial catheterization is more dangerous than venous but may achieve superior result by placing stimulation electrode (or electrodes) in close proximity to the renal nerve without surgery.

Figure 4:
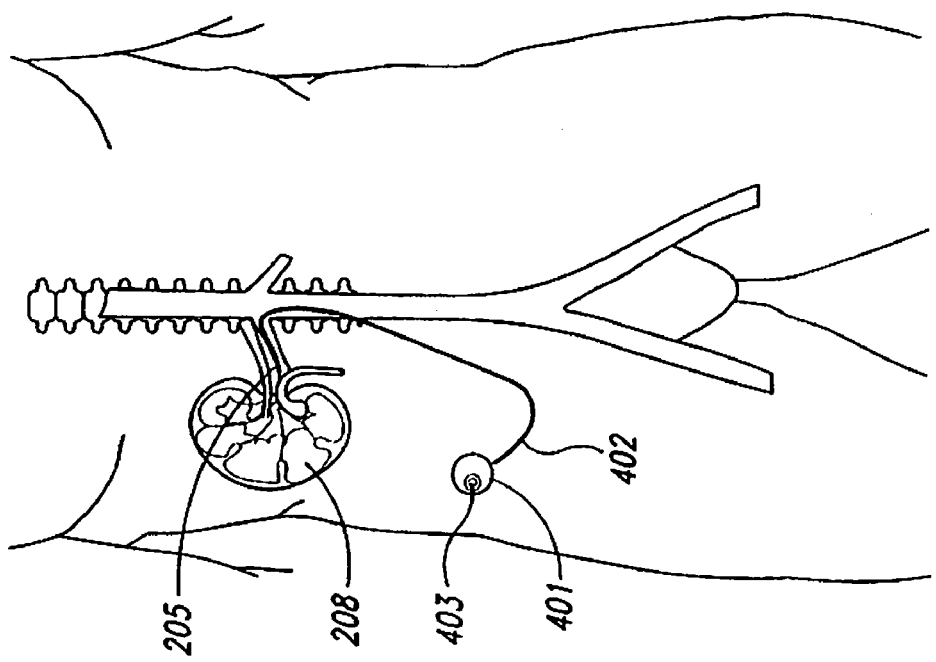
FIG. 4 illustrates the drug infusion blocking embodiment with an implanted drug pump.

FIG. 4 shows the use of a drug infusion pump 401 to block or partially block stimulation of the kidney 208 by infiltrating tissue proximal to the renal nerve 205 with a nerve-blocking drug. Pump 401 can be an implanted drug pump. The pump is equipped with a reservoir 403 and an access port (not shown) to refill the reservoir with the drug by puncturing the skin of the patient and the port septum with an infusion needle. The pump is connected to the infusion catheter 402 that is surgically implanted in the proximity of the renal nerve 205. The drug used in this embodiment can be a common local anesthetic such as Novocain. If it is desired to block the nerve for a long time after a single bolus drug infusion, a nerve toxin such as botox (botulism toxin) can be used as a nerve-blocking drug. Other suitable nerve desensitizing agents may comprise, for example, tetrodotoxin or other inhibitor of excitable tissues.

Figure 5:
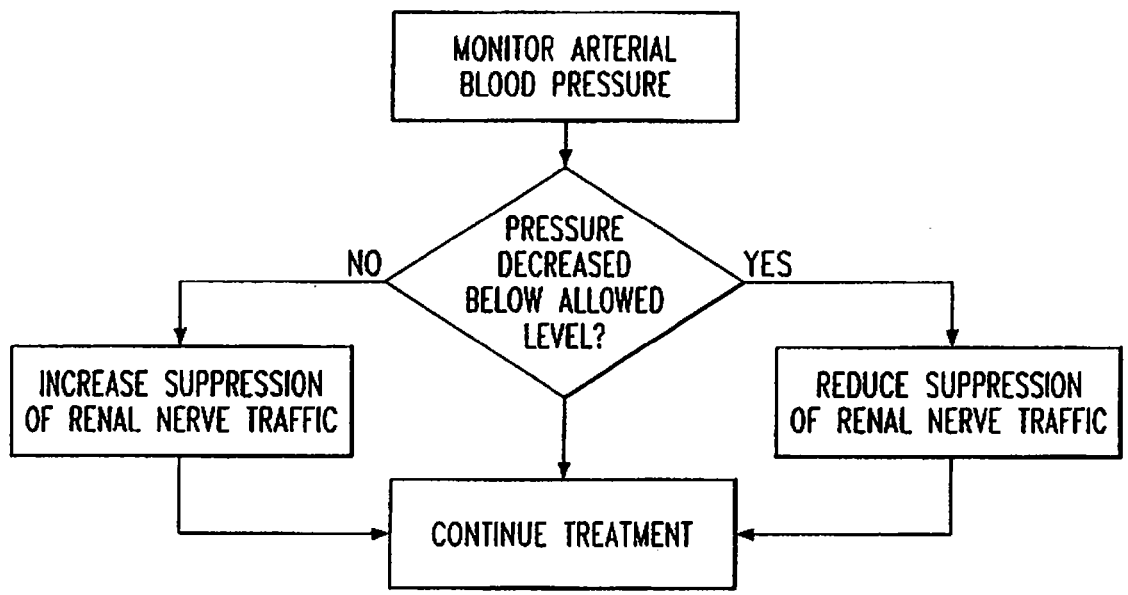
FIG. 5 illustrates the arterial pressure based control algorithm for renal nerve modulation.

FIG. 5 illustrates the use of arterial blood pressure monitoring to modulate the treatment of CHF with renal nerve blocking. The blood pressure is monitored by the computer controlled implanted device 202 (FIG. 2) using the implanted sensor 210. Alternatively the controlling device can be incorporated in the external nerve stimulator 306 (FIG. 3) and connected to a standard blood pressure measurement device (not shown). The objective of control is to avoid hypotension that can be caused by excessive vasodilation of renal arteries caused by suppression of renal sympathetic stimulus. This may cause the increase of renal blood flow dangerous for the heart failure patient with the limited heart pumping ability. The control algorithm increases or decreases the level of therapy with the goal of maintaining the blood pressure within the safe range. Similarly the oxygen content of venous or arterial blood can be measured and used to control therapy. Reduction of blood oxygen is an indicator of insufficient cardiac output in heart failure patients.

Figure 6:
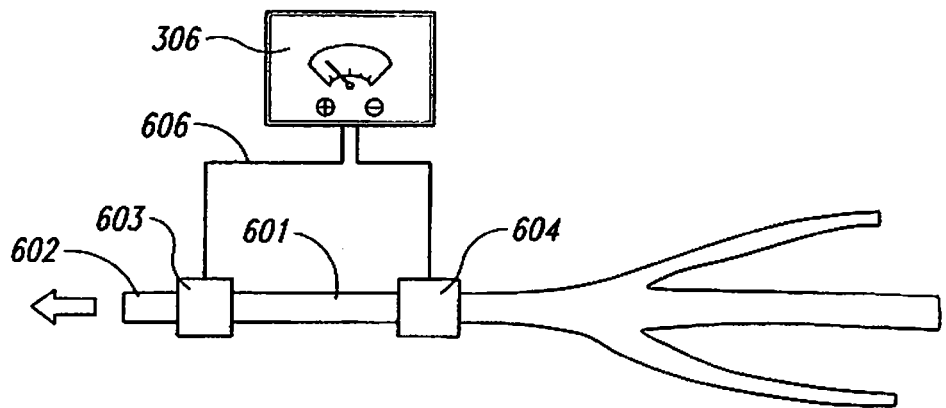
FIG. 6 illustrates electrostimulation of the renal nerve with an anodal block.

FIG. 6 illustrates the principles of modulating renal nerve signal with an anodal block. Renal nerve 601 conducts efferent sympathetic electric signals in the direction towards the kidney 602. Renal nerve 601 trunk is enveloped with two conductive cuff type electrodes: the anode 603 is a positive pole and the cathode 604 is a negative pole electrode. It is significant that the anode 603 is downstream of the cathode and closer to the kidney while the cathode is upstream of the anode and closer to the spine where the sympathetic nerve traffic is coming from. The electric current flowing between the electrodes opposes the normal propagation of nerve signals and creates a nerve block. Anode 603 and cathode 604 electrodes are connected to the signal generator (stimulator) 306 with wires 606. This embodiment has a practical application even if the device for renal nerve signal modulation is implanted surgically. During surgery the renal nerve is exposed and cuffs are placed that overlap the nerve. The wires and the stimulator can be fully implanted at the time of surgery. Alternatively wires or leads can cross the skin and connect to the signal generator outside of the body. An implantable stimulator can be implanted later during a separate surgery or the use of an external stimulator can be continued.

Clinically used spiral cuffs for connecting to a nerve are manufactured by Cyberonics Inc. (Houston, Tex.) that also manufactures a fully implantable nerve stimulator operating on batteries. See also, e.g., U.S. Pat. No. 5,251,643. Various external signal generators suitable for nerve stimulation are available from Grass-Telefactor Astro-Med Product Group (West Warwick, R.I.). Nerve cuff electrodes are well known. See, e.g., U.S. Pat. No. 6,366,815. The principle of the anodal block is based on the observation that close to an anodal electrode contact the propagation of a nerve action potential can be blocked due to hyperpolarization of the fiber membrane. See e.g., U.S. Pat. Nos. 5,814,079 and 5,800,464. If the membrane is sufficiently hyperpolarized, action potentials cannot pass the hyperpolarized zone and are annihilated.

As large diameter fibers need a smaller stimulus for their blocking than do small diameter fibers, a selective blockade of the large fibers is possible. See e.g., U.S. Pat. No. 5,755,750. The activity in different fibers of a nerve in an animal can be selectively blocked by applying direct electric current between an anode and a cathode attached to the nerve.

Antidromic pulse generating wave form for collision blocking is an alternative means of inducing a temporary electric blockade of signals traveling along nerve fibers. See e.g., U.S. Pat. No. 4,608,985. In general, nerve traffic manipulation techniques such as anodal blocking, cathodal blocking and collision blocking are sufficiently well described in scientific literature and are available to an expert in neurology. Most of blocking methods allow sufficient selectivity and reversibility so that the nerve will not be damaged in the process of blocking and that selective and gradual modulation or suppression of traffic in different functional fibers can be achieved.

A nerve is composed of the axons of a large number of individual nerve fibers. A large nerve, such as a renal nerve, may contain thousands of individual nerve fibers, both myelinated and non-myelinated Practical implementation of physiological blockade of selective nerve fibers in a living organism is illustrated by the paper "Respiratory responses to selective blockade of carotid sinus baroreceptors in the dog" by Francis Hopp. Both anodal block and local anesthesia by injection of bupivacaine (a common long-acting local anaesthetic, used for surgical anaesthesia and acute pain management) were applied to the surgically isolated and exposed but intact nerve leading from baroreceptors (physiologic pressure sensors) in the carotid sinus of the heart to the brain of an animal. Anodal block was induced using simple wire electrodes. Experiments showed that by increasing anodal blocking current from 50 to 350 microamperes signal conduction in C type fibers was gradually reduced from 100% to 0% (complete block) in linear proportion to the strength of the electric current. Similarly increasing concentration of injected bupivacaine (5, 10, 20 and 100 mg/ml) resulted in gradual blocking of the carotid sinus nerve activity in a dog. These experiments confirmed that it is possible to reduce intensity of nerve stimulation (nerve traffic) in an isolated nerve in controllable, reversible and gradual was by the application of electric current or chemical blockade. In the same paper it was described that smaller C type fibers were blocked by lower electric current and higher concentration of bupivacaine than larger C type fibers.

Gerald DiBona in "Neural control of the kidney: functionally specific renal sympathetic nerve fibers" described the structure and role of individual nerve fibers controlling the kidney function. Approximately 96% of sympathetic renal fibers in the renal nerve are slow conducting unmyelinated C type fibers 0.4 to 2.5 micrometers in diameter. Different fibers within this range carry different signals and respond to different levels of stimulation and inhibition. It is known that lower stimulation voltage of the renal nerve created untidiuretic effect (reduced urine output) while higher level of stimulation created vasoconstriction effect. Stimulation threshold is inversely proportional to the fiber diameter; therefore it is likely that elevated signal levels in larger diameter renal nerve C fibers are responsible for the retention of fluid in heart failure. Relatively smaller diameter C fibers are responsible for vasoconstriction resulting in the reduction of renal blood flow in heart failure.

Figure 7:
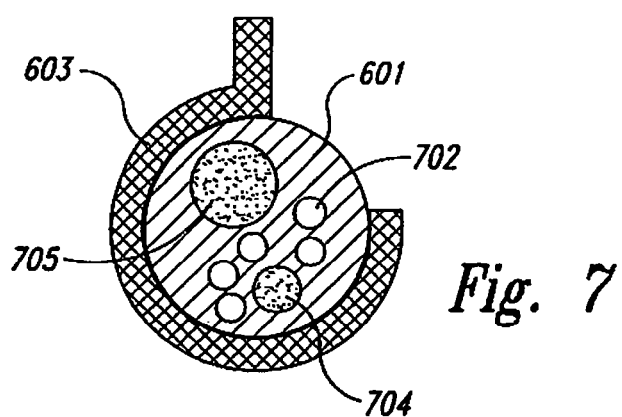
FIG. 7 illustrates different nerve fibers in a nerve bundle trunk.

FIG. 7 illustrates a simplified cross-section of the renal nerve trunk 601. Trunk 601 consists of a number of individual fibers. The stimulation electrode cuff 603 envelops the nerve trunk. Larger C type fiber 705 exemplifies fibers responsible for diuresis. There are also other fibers 702 that can be for example afferent fibers. Traffic along these fibers can be blocked by the application of lower blocking voltage or lower dose of anesthetic drug. The resulting effect will be diuresis of the CHF patient (secretion of sodium and water by the kidney) and the relief of fluid overload. Smaller C fiber 704 is responsible for the regulation of renal blood flow.

In clinical practice, it may be desired to modulate or block selectively or preferably the larger fibers 705. This can be achieved with lower levels of stimulation. The patient can be relieved of access fluid without significantly increasing renal blood flow since traffic in smaller C fibers will not be altered. Renal blood flow can amount to as much as 20% of cardiac output. In a CHF patient with a weakened heart significant increase of renal blood flow can lead to a dangerous decrease of arterial pressure if the diseased heart fails to pump harder to keep up with an increased demand for oxygenated blood.

The nerve stimulator or signal generator 306 therefore is capable of at least two levels of stimulation: first (lower) level to block or partially block signals propagating in larger C fibers that control diuresis, and second (higher) level to block signals propagating in smaller C fibers that control renal vascular resistance and blood flow to the kidney. The later method of nerve traffic modulation with higher electric current levels is useful in preventing damage to kidneys in acute clinical situations where the vasoconstriction can lead to the ischemia of a kidney, acute tubular necrosis (ATN), acute renal failure and sometimes permanent kidney damage. This type of clinical scenario is often associated with the acute heart failure when hypotension (low blood pressure) results from a severe decompensation of a chronic heart failure patient. Acute renal failure caused by low blood flow to the kidneys is the most costly complication in patients with heart failure.

Similar differentiated response to modulation could be elicited by applying different frequency of electric pulses (overpacing) to the renal nerve and keeping the applied voltage constant. DiBona noted that renal fibers responsible for rennin secretion responded to the lowest frequency of pulses (0.5 to 1 Hz), fibers responsible for sodium retention responded to middle range of frequencies (1 to 2 Hz) and fibers responsible for blood flow responded to the highest frequency of stimulation (2 to 5 Hz). This approach can be used when the renal nerve block is achieved by overpacing the renal nerve by applying rapid series of electric pulses to the electrodes with the intent to fatigue the nerve to the point when it stops conducting stimulation pulses.

One embodiment of the method of treating heart failure comprises the following steps:

A. Introducing one or more electrodes in the close proximity with the renal nerve, B. Connecting the electrodes to an electric stimulator or generator with conductive leads or wires, C. Initiating flow of electric current to the electrodes sufficient to block or reduce signal traffic in the sympathetic efferent renal nerve fibers with the intention of increasing diuresis, reducing renal secretion of renin and vasodilation of the blood vessels in the kidney to increase renal blood supply.

Figure 8:
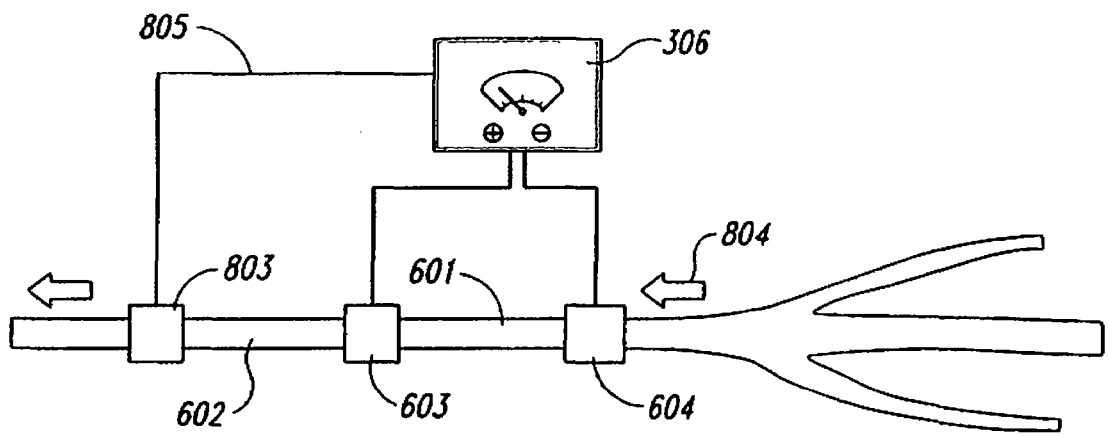
FIG. 8 illustrates renal nerve modulation by blocking electric signals at one point and stimulating the nerve at a different point.

FIG. 8 shows an alternative embodiment of the invention. In this embodiment the natural efferent signal traffic 804 entering the renal nerve trunk 601 is completely blocked by the anodal block device stimulator 306 using a pair of electrodes 604 and 603. The third electrode (or pair of electrodes) 803 is situated downstream of the block. The electrode is used to stimulate or pace the kidney. Stimulation signal is transmitted from the generator 306 via the additional lead wire 805 to the electrode 803. The induced signal becomes the nerve input to the kidney. This way full control of nerve input is accomplished while the natural sympathetic tone is totally abolished.

Figure 9:
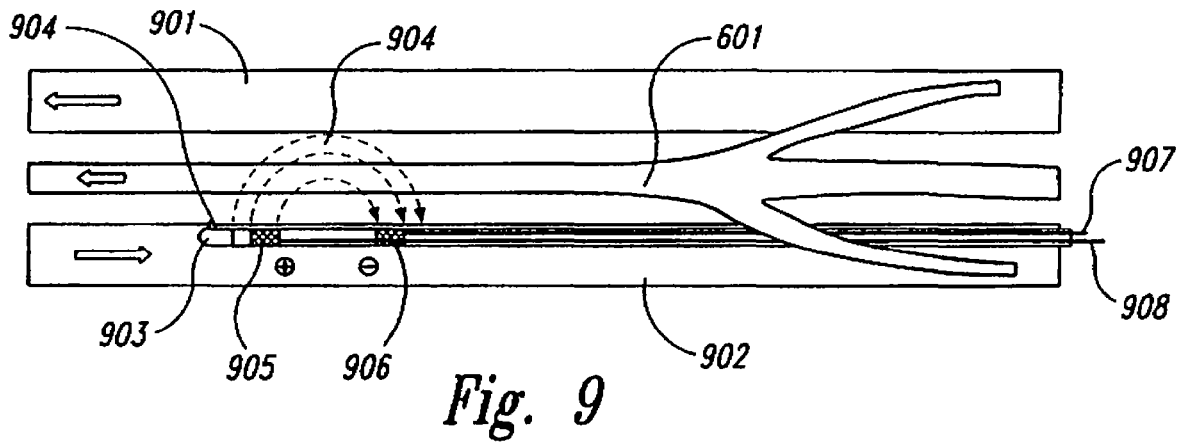
FIG. 9 illustrates transvenous stimulation of the renal nerve with electric field.

FIG. 9 shows the transvenous embodiment of the invention using anodal blockade to modulate renal nerve traffic. Renal nerve 601 is located between the renal artery 901 and the renal vein 902. It follows the same direction towards the kidney. Renal artery can branch before entering the kidney but in the majority of humans there is only one renal artery. Stimulation catheter or lead 903 is introduced into the renal vein 902 and anchored to the wall of the vein using a securing device 904. The securing device can be a barb or a screw if the permanent placement of the lead 903 is desired. Electric field 904 is induced by the electric current applied by the positively charged anode 905 and cathode 906 catheter electrodes. Electrodes are connected to the stimulator (nor shown) by wires 907 and 908 that can be incorporated into the trunk of the lead

903. Electric field 904 is induced in the tissue surrounding the renal vein 902 and created the desired local polarization of the segment of the renal nerve trunk 601 situated in the close proximity of the catheter electrodes 905 and 907. Similarly catheters or leads can be designed that induce a cathodal block, a collision block or fatigue the nerve by rapidly pacing it using an induced field rather than by contacting the nerve directly.

Figure 10:
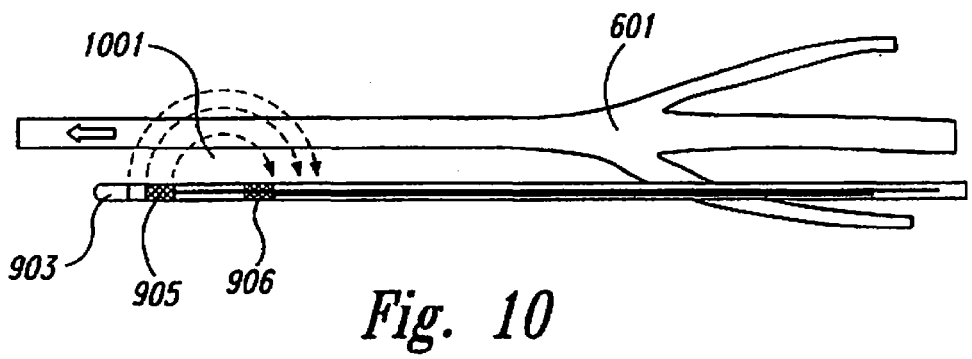
FIG. 10 illustrates an embodiment where the stimulation lead is placed using laparoscopic surgery.

FIG. 10 shows an embodiment where the stimulation lead is placed using laparoscopic surgery. This technology is common in modern surgery and uses a small video-camera and a few customized instruments to perform surgery with minimal tissue injury. The camera and instruments are inserted into the abdomen through small skin cuts allowing the surgeon to explore the whole cavity without the need of making large standard openings dividing skin and muscle.

After the cut is made in the umbilical area a special needle is inserted to start insufflation. A pressure regulated CO2 insufflator is connected to the needle. After satisfactory insufflation the needle is removed and a trocar is inserted through the previous small wound. This method reduces the recovery time due to its minimal tissue damage permitting the patient to return to normal activity in a shorter period of time. Although this type of procedure is known since the beginning of the 19th. century, it was not until the advent of high resolution video camera that laparoscopic surgery became very popular among surgeons. Kidney surgery including removal of donor kidneys is routinely done using laparoscopic methodology. It should be easy for a skilled surgeon to place the lead 903 through a tunnel in tissue layers 1001 surrounding the renal nerve 601. This way lead electrodes 905 and 906 are placed in close proximity to the nerve and can be used to induce a block without major surgery.

Figure 11:
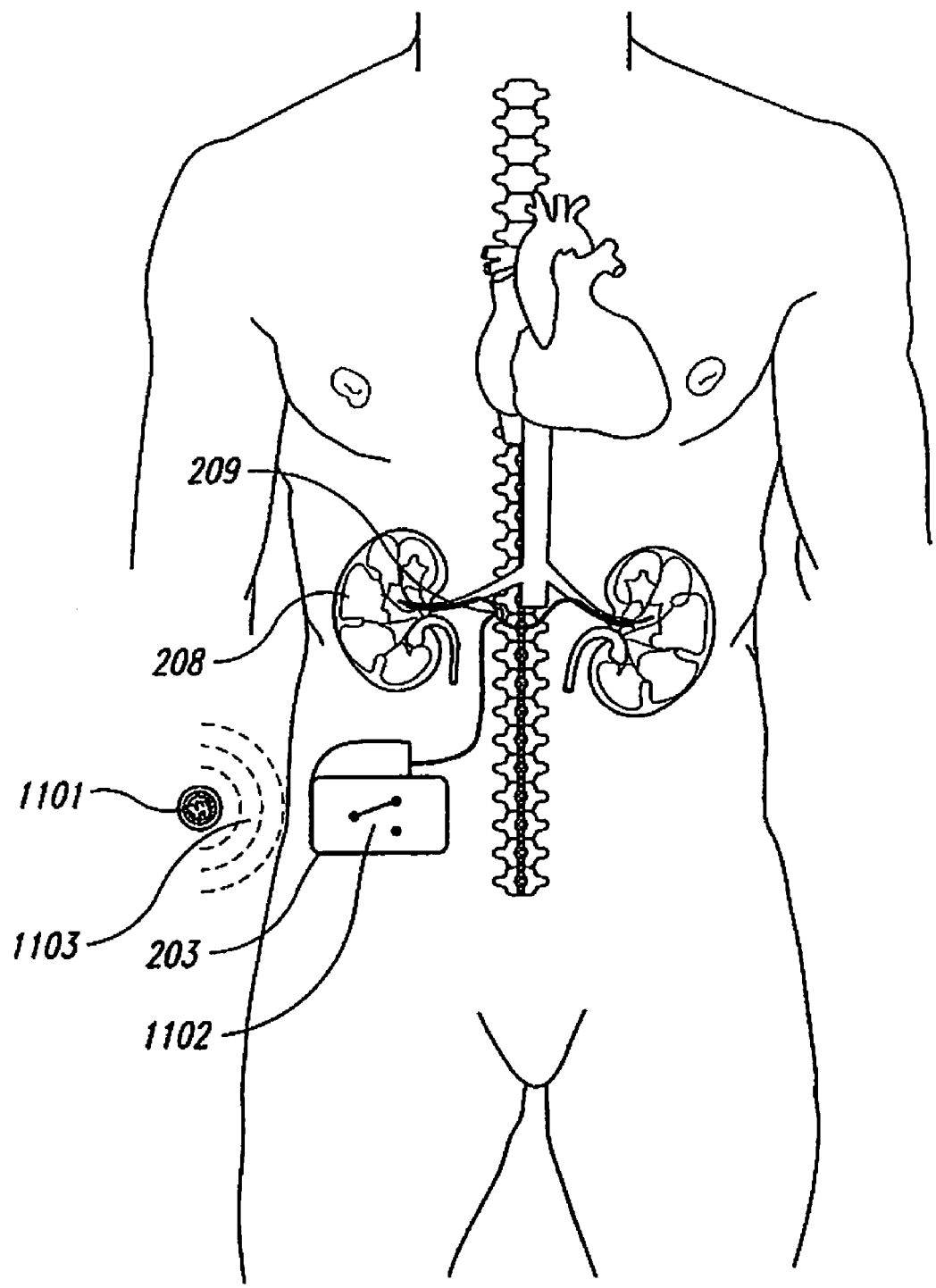
FIG. 11 illustrates a patient controlled stimulation embodiment.

FIG. 11 shows an implanted embodiment of the invention controlled by the patient from outside of the body. The implanted stimulation device 203 is an electric stimulation device to modulate the renal nerve signal but can be an implantable infusion pump capable of infusing a dose of an anesthetic drug on command. The implantable device 203 incorporates a magnetically activated switch such as a reed relay. The reed switch can be a single-pole, single-throw (SPST) type having normally open contacts and containing two reeds that can be magnetically actuated by an electromagnet, permanent magnet or combination of both. Such switch of extremely small size and low power requirements suitable for an implanted device is available from Coto Technology of Providence, R.I. in several configurations. Switch is normally open preventing electric or chemical blockade of the renal nerve 209. When the patient brings a magnet 1101 in close proximity to the body site where the device 202 is implanted the magnetic field 1103 acts on the magnetic switch 1102. Switch is closed and blocking of the renal nerve is activated. The resulting reduction of the sympathetic tone commands the kidney 208 to increase the production of urine. Patient can use the device when they feel the symptoms of fluid overload to remove access fluid from the body. The device 202 can be equipped with a timing circuit that is set by the external magnet. After the activation by the magnet the device can stay active (block renal nerve activity) for a predetermined duration of time to allow the kidney to make a desired amount of urine such as for an hour or several hours. Then the device will time out to avoid excessive fluid removal or adaptation of the renal nerve to the new condition.

Figure 12:
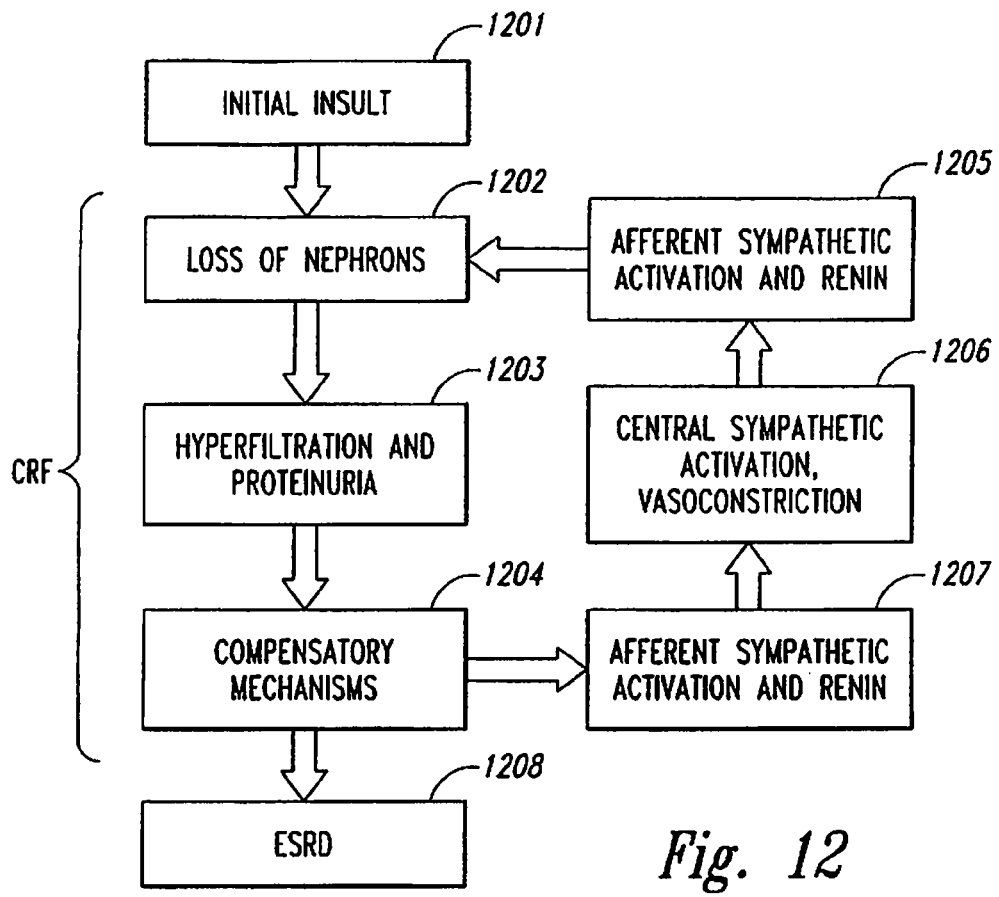
FIG. 12 illustrates the progression of CRF to ESRD.

FIG. 12 illustrates the progression of CRF to ESRD. Following the original injury to the kidney 1201 some nephrons 1202 are lost. Loss of nephrons lead to hyperfiltration 1203 and triggers compensatory mechanisms 1204 that are initially beneficial but over time make injury worse until the ESRD 1208 occurs. Compensatory mechanisms lead to elevated afferent and efferent sympathetic nerve signal level (increased signal traffic) 1207 to and from the kidney. It is the objective of this invention to block, reduce, modulate or otherwise decrease this level of stimulation.

The effect of the invented therapeutic intervention will be the reduction of central (coming from the brain) sympathetic stimulation 1206 to all organs and particularly blood vessels that causes vasoconstriction and elevation of blood pressure. Following that hypertension 1205 will be reduced therefore reducing continuous additional insult to the kidney and other organs.

Figure 13:
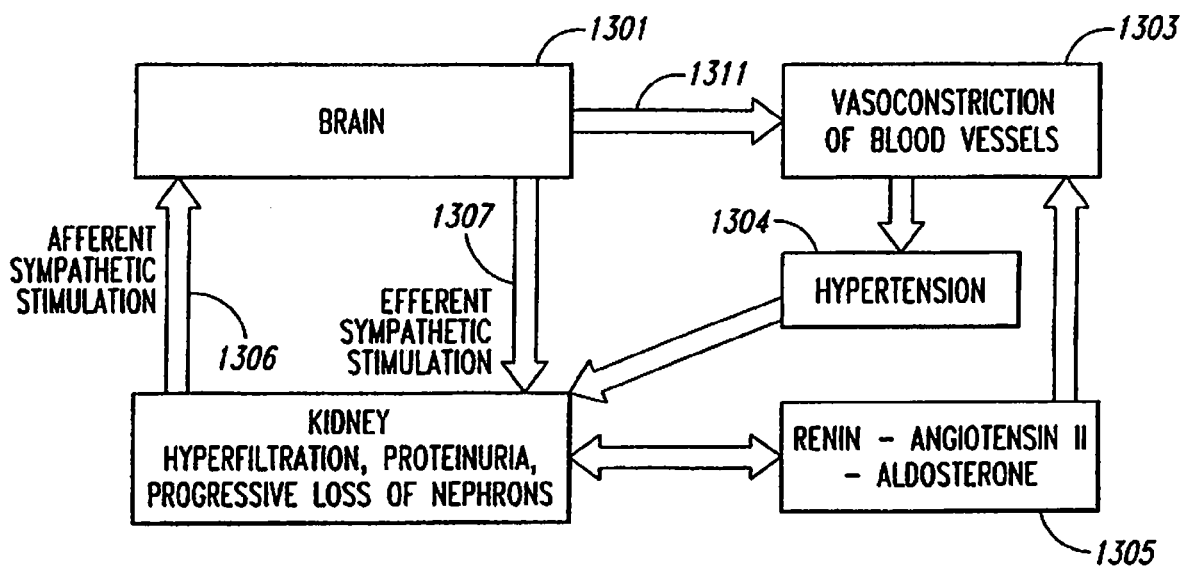
FIG. 13 illustrates the physiologic mechanisms of CRF.

FIG. 13 illustrates the physiologic mechanisms of CRF and hypertension. Injured kidney 1302 sends elevated afferent nerve 1306 signals to the brain 1301. Brain in response increases sympathetic efferent signals to the kidney 1307 and to blood vessels 1311 that increase vascular resistance 1303 by vasoconstriction. Vasoconstriction 1303 causes hypertension 1304. Kidney 1302 secretes renin 1310 that stimulates production of the vasoconstrictor hormone Angiotensin II 1305 that increases vasoconstriction of blood vessels 1303 and further increases hypertension 1304. Hypertension causes further mechanical damage 1312 to the kidney 1302 while sympathetically activated neurohormones 1307 and angiotensin II causes more subtle injury via the hormonal pathway 1310.

Invented therapy reduces or eliminates critical pathways of the progressive disease by blocking afferent 1306 and efferent 1307 signals to and from the kidney 1302. Both neurological 1311 and hormonal 1309 stimulus of vasoconstriction are therefore reduced resulting in the relief of hypertension 1304. As a result, over time the progression of renal disease is slowed down, kidney function is improved and the possibility of stroke from high blood pressure is reduced.

Figure 14:
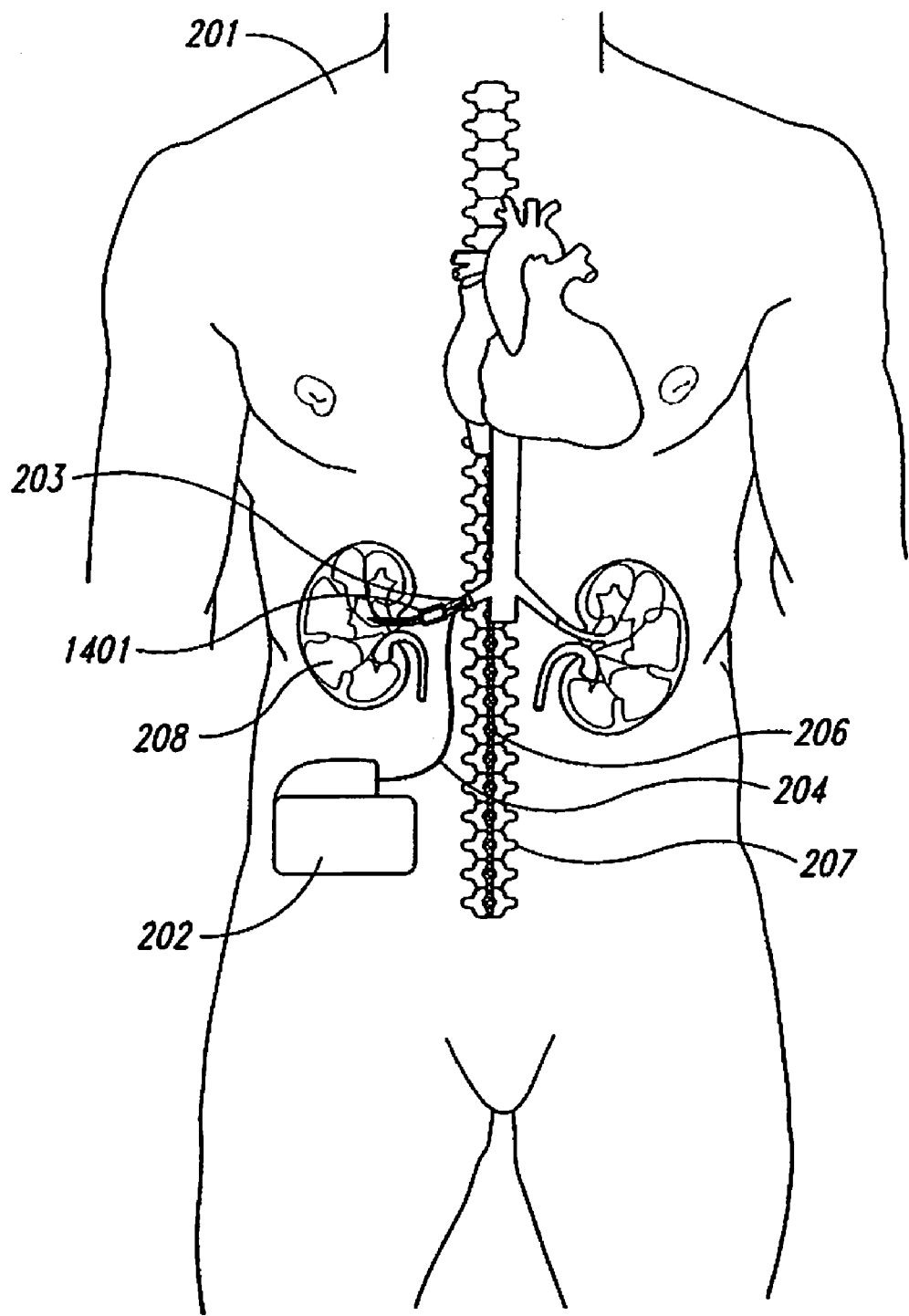
FIG. 14 illustrates stimulation of renal nerves in a patient with an implanted stimulator with a renal artery cuff electrode.

FIG. 14 shows a patient 201 suffering from CRF or renal hypertension treated in accordance with the invention. An implanted device 202 is implanted in the patient's body. An implantable device can be an electric nerve stimulator or a chemical substance (drug) infusion device. The implantable device 202 described above is equipped with the lead 204 connecting it to the renal nerve artery cuff 1401. Cuff 1401 envelopes the renal artery 203 that anatomically serves as a support structure for the renal nerve plexus. It is understood that there exist many varieties of electrode configurations such as wires, rings, needles, anchors, screws, cuffs and hooks that could all potentially be used to stimulate renal nerves. The cuff configuration 1401 illustrated by FIGS. 14, 15, 16 and 17 was selected for the preferred embodiment base on the information available to the inventors at the time of invention.

The lead conduit can be alternatively an electric wire or a catheter for delivery of medication or a combination of both. Renal nerve conducts efferent sympathetic stimulation from the sympathetic trunk 206 to the kidney 208. Sympathetic trunk is connected to the patient's spinal cord inside the spine 207. The lead to nerve connection can be located anywhere between the kidney 208 and the posterior renal or other renal ganglia (not shown) in the region of the $10^{th}$, $11^{th}$ and $12^{th}$ thoracic and $1^{st}$ lumbar segments of the spine 207. The stimulation lead 204 and the arterial nerve cuff 1401, as selected for the preferred embodiment of the invention, can be placed using laparoscopic surgery.

Figure 15:
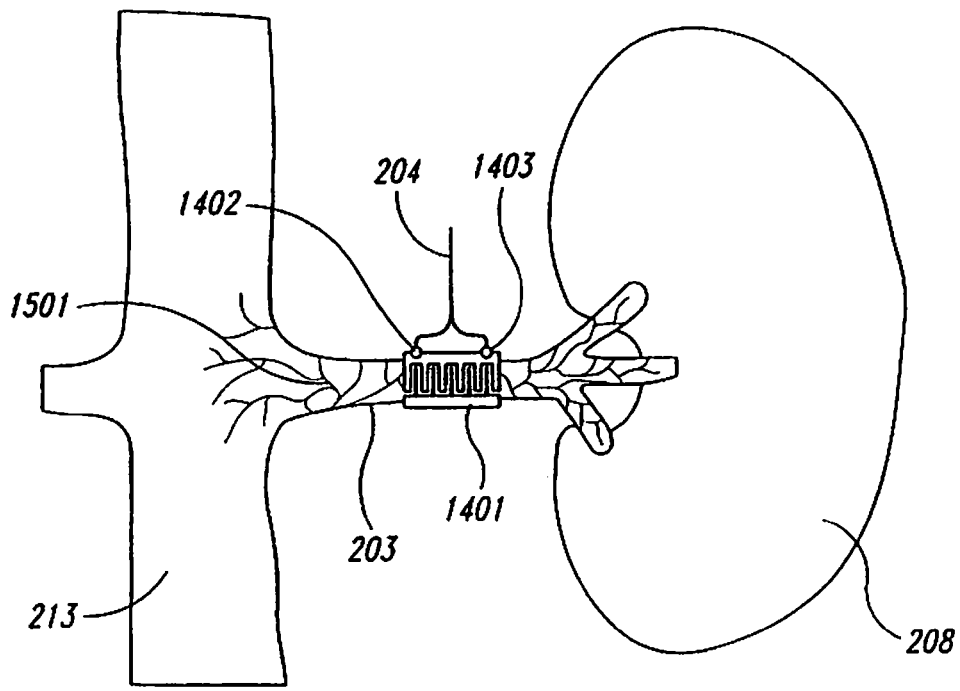
FIG. 15 illustrates the placement of a stimulation cuff on a renal artery end nerve plexus.

FIG. 15 illustrates one possible embodiment of the renal nerve stimulation cuff electrode cuff. When the treated disease is CRF or hypertension it is the additional objective of this embodiment of the invention to selectively modulate nerve traffic in both afferent and efferent nerve fibers innervating the human kidney. Using existing selective modulation techniques it is possible to stimulate only afferent or efferent fibers. Different types of fibers have different structure and respond to different levels and frequency of stimulation. Anatomically renal nerve is difficult to locate in humans even during surgery. The autonomic nervous system forms a plexus on the external surface renal artery. Fibers contributing to the plexus arise from the celiac ganglion, the lowest splanchnic nerve, the aorticorenal ganglion and aortic plexus. The plexus is distributed with branches of the renal artery to vessels of the kidney, the glomeruli and tubules. The nerves from these sources, fifteen or twenty in number, have a few ganglia developed upon them. They accompany the branches of the renal artery into the kidney; some filaments are distributed to the spermatic plexus and, on the right side, to the inferior vena cava. This makes isolating a renal nerve difficult.

To overcome this anatomic limitation the preferred embodiment of the neurostimulation shown on FIG. 15 has an innovative stimulation cuff. The cuff 1401 envelopes the renal artery 203 and overlaps nerve fibers 1501 that form the renal plexus and look like a spider web. Cuff has at least two isolated electrodes 1402 and 1403 needed for nerve blocking. More electrodes can be used for selective patterns of stimulation and blocking. Electrodes are connected to the lead 204. Renal artery 203 connects aorta 213 to the kidney 208. It is subject to pulsations of pressure and therefore cyclically swells and contracts.

Figure 16:
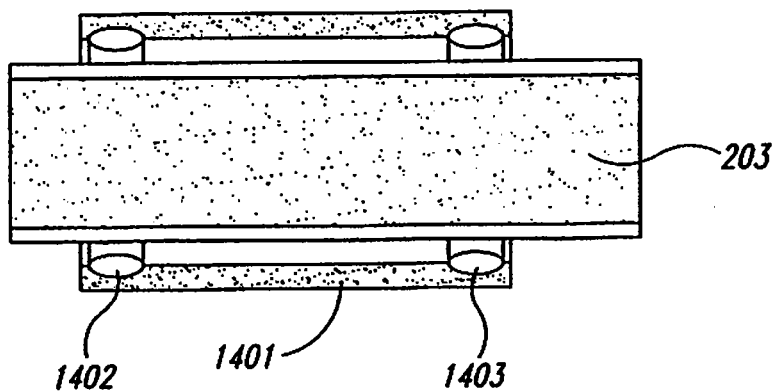
FIG. 16 illustrates the design of the cuff electrode that wraps around an artery.

FIG. 16 further illustrates the design of the cuff 1401. Cuff envelopes the renal artery 203. Cuff is almost circumferential but has an opening 406. When the artery cyclically swells with blood pressure pulses, the cuff opens up without damaging the nerve or pinching the artery. Opening 406 also allows placement of the cuff around the artery. Similar designs of nerve cuffs known as "helical" cuffs are well known, see e.g., U.S. Pat. Nos. 5,251,634; 4,649,936 and 5,634,462.

Figure 17:
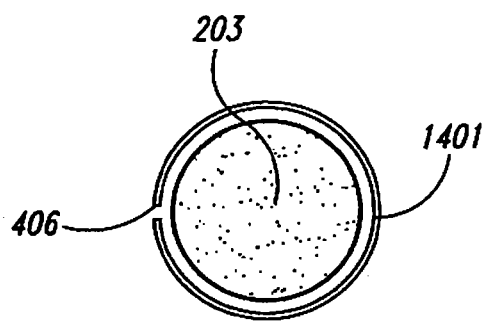
FIG. 17 illustrates the interface between cuff electrodes and the renal artery surface.

FIG. 17 shows the crossection of the cuff 1401. Cuff 1401 is made out of dielectric material. Two electrodes 1402 and 1403 form rings to maximize the contact area with the wall of the artery 203.

Common to all the embodiments, is that an invasive device is used to decrease the level of renal nerve signals that are received by the kidney or generated by the kidney and received by the brain. The invention has been described in connection with the best mode now known to the applicant inventors. The invention is not to be limited to the disclosed embodiment. Rather, the invention covers all of various modifications and equivalent arrangements included within the spirit and scope of the appended claims.

Heart failure, also called congestive heart failure (CHF) and chronic heart failure is a progressive heart disease characterized by low cardiac output, deterioration of heart muscle and fluid retention. Renal failure, also called chronic renal failure (CRF) is a progressive degenerative renal disease that is characterized by gradual loss of renal function that leads to the end stage renal disease (ESRD). ESRD requires dialysis for life. Hypertension is the chronic disease associated with high probability of stroke, renal failure and heart failure that is characterized by the abnormally high blood pressure.

A nerve in the context of this application means a separate nerve or a nerve bundle, nerve fiber, nerve plexus or nerve ganglion. Renal nerve is a part of the autonomic nervous system that forms a plexus on the external surface renal artery. Fibers contributing to the plexus arise from the celiac ganglion, the lowest splanchnic nerve, the aorticorenal ganglion and aortic plexus. The plexus is distributed with branches of the renal artery to blood vessels of the kidney, the glomeruli and tubules. The nerves from these sources, have a few ganglia developed upon them. They accompany the branches of the renal artery into the kidney; some filaments are distributed to the spermatic plexus and, on the right side, to the inferior vena cava.

Nerve stimulation, neurostimulation, nerve modulation and neuromodulation are equivalent and mean altering (reducing or increasing) naturally occurring level of electric signals propagating through the nerve. The electric signal in the nerve is also called nerve traffic, nerve tone or nerve stimulus.

Nerve block, blocking or blockade is a form of neuromodulation and means the reduction or total termination of the propagation or conduction of the electric signal along the selected nerve. Nerve block can be pharmacological (induced by a drug or other chemical substance) or an electric block by electrostimulation. Electric nerve block can be a hyperpolarization block, cathodal, anodal or collision block. Overpacing a nerve can also induce a block. Overpacing means stimulating the nerve with rapid electric pulses at a rate that exceeds the natural cycling rate of the nerve polarization and depolarization. As a result of overpacing the nerve gets fatigued, reserves of the immediately available neurotransmitter substance in the nerve become exhausted, and the nerve becomes temporarily unable to conduct signals. Nerve block by the means listed above can result in the reduction of the nerve signal, in particular the renal sympathetic efferent or afferent tone that determines the electric stimulus received or generated by the kidney. The technique of the controlled reduction of the nerve signal or traffic, which results in less organ stimulation, is called nerve signal modulation. Nerve modulation means that the individual nerve fibers fire with a reduced frequency or that fewer of the nerve fibers comprising the renal nerve are actively conducting or firing. The increase of nerve traffic or nerve activity usually involves recruitment of larger number of fibers in the nerve; alternatively less stimulation is associated with less active fibers. Denervation means blocking of the renal nerve conduction or the destruction of the renal nerve.

Lead is a medical device used to access the nerve designated for stimulation or blocking. It is usually a tubular device that is electrically insulated and includes multiple conductors or wires. Wires conduct stimulation or blocking signals from the stimulator to the designated nerve. Wires are terminated in electrodes. Electrodes are conductive terminals and can contact the nerve directly or contact the conductive tissue in the vicinity of the nerve. Electrodes can have different geometric configurations and can be made of different materials. The lead can include lumens or tubes for drug delivery to the nerve. A stimulator or an electrostimulator is an electric device used to generate electric signals that are conducted by the lead to the nerve. The stimulator can be implanted in the body or external. Electric signals can be a DC current, voltage, series of pulses or AC current or voltage. Electrodes can induce an electric field that affects the nerve and results in nerve blocking. Nerve cuff is a support structure that at least partially envelops the targeted nerve.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of treating a patient diagnosed with at least one of heart failure, hypertension, acute myocardial infarction, renal disease, or chronic renal failure, the method of treating the patient comprising:
   positioning an electrode proximate to post-ganglionic neural fibers that innervate a kidney of the patient; and
   generating an electric field via the electrode such that at least a portion of the neural fibers are in the electric field, wherein the electric field reduces neural communication along the neural fibers.

2. The method of claim 1 wherein the neural fibers comprise a renal nerve, and wherein the electric field impedes neural activity along a portion of the renal nerve.

3. The method of claim 1 wherein the electric field alters at least one of urine production, fluid retention, renin secretion, waste excretion, sodium retention, systemic vasoconstriction, renal function, heart function and blood pressure in the patient.

4. The method of claim 1, further comprising removing the electrode from the patient.

5. The method of claim 1 wherein positioning the electrode proximate to post-ganglionic neural fibers that innervate a kidney further comprises positioning the electrode proximate to a renal nerve.

6. The method of claim 5 further comprising placing the electrode in a renal vessel proximate to the renal nerve.

7. The method of claim 6 wherein the electrode further comprises an anode and a cathode, and wherein placing the electrode further comprises placing the anode and cathode in the renal vessel proximate to the renal nerve.

8. The method of claim 6 wherein placing the electrode in a renal blood vessel further comprises placing the electrode in a renal artery of the patient.

9. The method of claim 6 wherein the renal nerve has a longitudinal section, and wherein at least a portion of the electric field extends along the longitudinal section.

10. The method of claim 9 wherein a longitudinal dimension of the electric field extends in a generally medial or generally lateral direction relative to the patient.

11. The method of claim 6 wherein placing the electrode in the renal vessel further comprises placing the electrode in contact with a wall of the renal vessel.

12. The method of claim 6 wherein the electrode further comprises an anode and a cathode.

13. The method of claim 6 wherein the renal nerve has a longitudinal section, and wherein a portion of the electric field extends along the longitudinal section.

14. The method of claim 13 wherein a longitudinal dimension of the electric field extends in a generally medial or generally lateral direction relative to the patient.

15. The method of claim 5 wherein the electrode comprises an anode and a cathode, and wherein the method further comprise passing an electric current from the anode to the cathode to impede neural activity along the renal nerve.

16. The method of claim 15 wherein the electric current from the anode to the cathode blocks efferent neural activity along the renal nerve.

17. The method of claim 15 wherein the electrical current from the anode to the cathode blocks afferent neural activity.

18. The method of claim 15 wherein the electrical current from the anode to the cathode blocks at least one of efferent and afferent neural activity.

19. The method of claim 5, wherein positioning the electrode comprises implanting the electrode in a vessel near the renal nerve of the patient by fixing the electrode to the vessel.

20. The method of claim 19, wherein implanting the electrode further comprises implanting an anode and a cathode in the vessel near the renal nerve of the patient by attaching the anode and cathode to the vessel.

21. The method of claim 5 wherein positioning the electrode comprises fixing the electrode in tissue near the renal nerve of the patient.

22. The method of claim 21 wherein fixing the electrode further comprises fixing an anode and a cathode in tissue near the renal nerve of the patient.

23. The method of claim 5 wherein positioning the electrode comprises inserting a catheter having the electrode into a vessel such that the electrode is proximate to the renal nerve of the patient.

24. The method of claim 23 wherein the electrode further comprises an anode and a cathode, and wherein inserting the catheter further comprises inserting the catheter into the vessel such that the anode and the cathode are proximate to the renal nerve of the patient.

25. The method of claim 23, further comprising:
   terminating the electric field; and
   removing the catheter from the patient after terminating the electric field.

26. The method of claim 5 wherein positioning the electrode comprises inserting a device having the electrode into tissue of the patient such that the electrode is adjacent to the renal nerve of the patient.

27. The method of claim 26 wherein the electrode further comprises an anode and a cathode, and wherein inserting the device further comprises inserting the device into tissue of the patient such that the anode and the cathode are adjacent to the renal nerve of the patient.

28. The method of claim 26, further comprising:
   terminating the electric field; and
   removing the device from the patient after terminating the electric field.

29. The method of claim 26 wherein the electrode at least partially encircles the renal nerve.

30. The method of claim 1 wherein the electrode further comprises an anode and a cathode.

31. The method of claim 30 further comprising placing the electrode such that the anode is between a kidney of the patient and the cathode.

32. The method of claim 30 further comprising arranging the anode and cathode to produce an anodal nerve block.

33. The method of claim 30 further comprising arranging the anode and cathode to produce a cathodal nerve block.

34. The method of claim 1 wherein:
   the neural fibers comprise a renal nerve having a longitudinal section; and
   at least a portion of the electric field extends along the longitudinal section of the renal nerve.

35. The method of claim 1, further comprising sensing a physiological parameter.

36. The method of claim 35 wherein the physiological parameter is at least one of blood pressure, blood flow, blood oxygen, cardiac output, and cardiac pulses.

37. The method of claim 35, further comprising modulating the electric field in response to the sensed physiological parameter.

38. The method of claim 1, wherein the electric field is arranged relative to the neural fibers such that current in the electric field travels in a direction opposite to efferent signals in the neural fibers.

39. The method of claim 1, wherein the electric field is arranged relative to the neural fibers such that current in the electric field travels in a direction opposite to afferent signals in the neural fibers.

40. The method of claim 1 wherein generating the electric field comprises selecting a parameter of the electric field such that neural activity along a first nerve fiber having a first size is at least substantially inhibited without substantially affecting neural activity along a second nerve fiber having a second size different than the first size.

41. The method of claim 40 wherein the parameter of the electric field is selected from at least one of frequency, field strength, pulse width and duty cycle.

42. The method of claim 1 wherein the electric field ablates at least one neural fiber.

43. The method of claim 1 wherein the electric field alters afferent neural activity across the neural fibers.

44. The method of claim 1 wherein the electric field alters efferent neural activity across the neural fibers.

45. The method of claim 1 wherein the electric field alters at least one of efferent and afferent neural activity across the neural fibers.

46. A method of treating a patient diagnosed with at least one of heart failure, hypertension, acute myocardial infarction, renal disease, or chronic renal failure, the method of treating the patient comprising:

positioning an electrode at least proximate to a renal nerve of a patient; and applying an electric field to the renal nerve via the electrode in a manner that inhibits neural activity along the renal nerve.

47. The method of claim 46 wherein the neural activity comprises efferent neural signals.

48. The method of claim 46 wherein the neural activity comprises afferent activity along a portion of the renal nerve.

49. The method of claim 46 wherein the neural activity comprises at least one of efferent and afferent activity along a portion of the renal nerve.

50. The method of claim 46 further comprising placing the electrode in a blood vessel proximate to the renal nerve.

51. The method of claim 50 wherein placing the electrode in a blood vessel further comprises placing the electrode in a renal artery.

52. The method of claim 51 wherein positioning the electrode comprises advancing a catheter having the electrode into the renal artery such that electrode is proximate to the renal nerve.

53. The method of claim 52 wherein advancing the catheter having the electrode into the renal artery such that electrode is proximate to the renal nerve further comprises positioning the electrode in contact with a wall of the renal artery.

* * * * *

UNITED STATES PATENT AND TRADEMARK OFFICE
CERTIFICATE OF CORRECTION

PATENT NO.        : 7,647,115 B2                                    Page 1 of 1
APPLICATION NO.   : 11/144173
DATED             : January 12, 2010
INVENTOR(S)       : Levin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 783 days.

Signed and Sealed this

Sixteenth Day of November, 2010

David J. Kappos
*Director of the United States Patent and Trademark Office*

(12) INTER PARTES REEXAMINATION CERTIFICATE (1282nd)
United States Patent
Levin et al.

(10) Number: US 7,647,115 C1
(45) Certificate Issued: *Jun. 13, 2016

(54) RENAL NERVE STIMULATION METHOD AND APPARATUS FOR TREATMENT OF PATIENTS

(75) Inventors: Howard R. Levin, Teaneck, NJ (US); Mark Gelfand, New York, NY (US)

(73) Assignee: ARDIAN, INC., Palo Alto, CA (US)

Reexamination Request:
No. 95/002,336, Sep. 14, 2012

Reexamination Certificate for:
Patent No.: 7,647,115
Issued: Jan. 12, 2010
Appl. No.: 11/144,173
Filed: Jun. 3, 2005

Certificate of Correction issued Nov. 16, 2010

( * ) Notice: This patent is subject to a terminal disclaimer.

Related U.S. Application Data

(63) Continuation of application No. 10/408,665, filed on Apr. 8, 2003, now Pat. No. 7,162,303.

(60) Provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61N 1/00* (2006.01)
*A61N 1/36* (2006.01)

(52) U.S. Cl.
CPC .............. *A61N 1/36* (2013.01); *A61N 1/36117* (2013.01)

(58) Field of Classification Search
None
See application file for complete search history.

(56) References Cited

To view the complete listing of prior art documents cited during the proceeding for Reexamination Control Number 95/002,336, please refer to the USPTO's public Patent Application Information Retrieval (PAIR) system under the Display References tab.

*Primary Examiner* — Beverly M Flanagan

(57) ABSTRACT

A method and apparatus for treatment of heart failure, hypertension and renal failure by stimulating the renal nerve. The goal of therapy is to reduce sympathetic activity of the renal nerve. Therapy is accomplished by at least partially blocking the nerve with drug infusion or electrostimulation. Apparatus can be permanently implanted or catheter based.

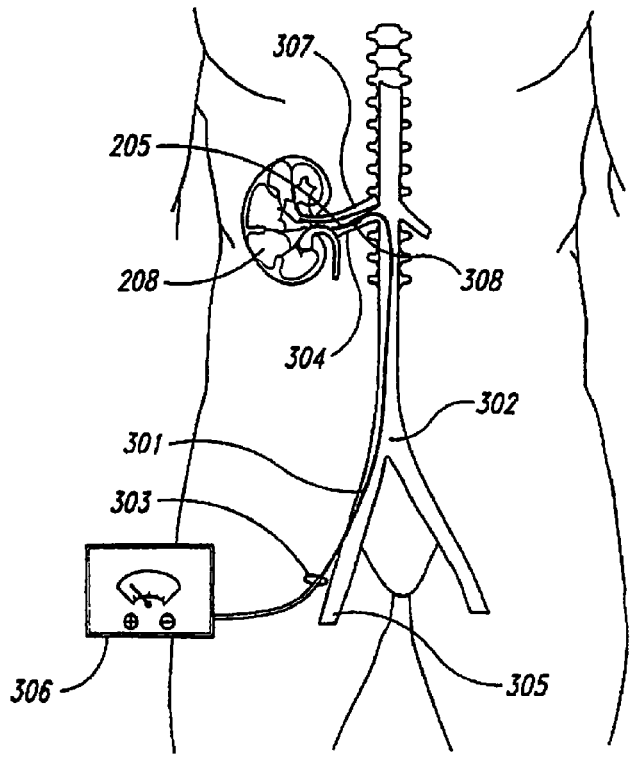

INTER PARTES REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1, 5-6, 8, 42 and 46 are cancelled.
Claims 2-4, 7, 9-41, 43-45 and 47-53 were not reexamined.

\* \* \* \* \*